United States Patent [19]

Vögtle et al.

[11] Patent Number: 4,853,151

[45] Date of Patent: Aug. 1, 1989

[54] DISPIROTETRADECANES

[75] Inventors: Fritz Vögtle, Alfter; Wolfgang Calaminus, Königswinter, both of Fed. Rep. of Germany

[73] Assignee: Merck Patent Gesellschaft Mit Beschrankfter Haftung, Darmstadt, Fed. Rep. of Germany

[21] Appl. No.: 112,356

[22] PCT Filed: Dec. 8, 1986

[86] PCT No.: PCT/EP86/00722

§ 371 Date: Aug. 11, 1987

§ 102(e) Date: Aug. 11, 1987

[87] PCT Pub. No.: WO87/03581

PCT Pub. Date: Jun. 18, 1987

[30] Foreign Application Priority Data

Dec. 13, 1985 [DE] Fed. Rep. of Germany ....... 3543997

[51] Int. Cl.$^4$ ............ C09K 19/32; C07C 43/18; C07C 121/46; C07C 13/72; C07C 23/18; C07C 49/385; C07C 49/587; C07C 43/21
[52] U.S. Cl. ............ 252/299.61; 252/299.5; 252/299.63; 350/350 R; 544/179; 544/182; 544/230; 546/15; 549/20; 549/21; 549/22; 549/13; 549/14; 549/28; 549/330; 558/17; 558/265; 558/266; 558/267; 558/268; 558/269; 558/270; 558/271; 558/273; 558/275; 558/276; 558/384; 560/20; 560/21; 560/59; 560/60; 560/64; 560/73; 560/102; 560/104; 560/105; 560/106; 560/107; 560/108; 560/116; 560/8; 560/138; 560/141; 560/1; 560/174; 560/183; 560/187; 560/188; 560/220; 560/221; 560/255; 560/256; 568/326; 568/329; 568/367; 568/368; 568/585; 568/583; 568/631; 568/632; 568/634; 568/642; 568/659; 568/661; 568/664; 568/665; 568/928; 568/929; 568/931; 568/930; 568/941; 568/942; 570/128; 570/129; 570/130; 570/182; 570/183; 570/187; 570/188; 585/20; 585/22
[58] Field of Search ............ 252/299.63, 299.62, 252/299.5, 299.61; 350/350 R; 544/179, 182, 230; 546/15; 549/20, 21, 22, 13, 14, 28, 330; 558/17, 265, 266, 267, 268, 269, 270, 271, 273, 275, 276, 384; 560/20, 21, 59, 60, 64, 73, 102, 104, 105, 106, 107, 108, 116, 8, 138, 141, 1, 174, 183, 187, 188, 220, 221, 255, 256; 570/128, 129, 130, 182, 183, 187, 188

[56] References Cited

FOREIGN PATENT DOCUMENTS 59-152343 8/1984 Japan ..................... 252/299.63
2155946 10/1985 United Kingdom .......... 252/299.63

OTHER PUBLICATIONS

Calaminus, W., et al., Z. Naturforsch, vol. 416, pp. 1011–1014 (1986).
Franke, V., et al., Angew. Makromol. Chemie., vol. 21, pp. 195–205 (1972).
Farina, M., et al., Tetrahedron Letters, No. 3, pp. 183–186 (1975).

Primary Examiner—Teddy S. Gron
Attorney, Agent, or Firm—Millen, White & Zelano

[57] ABSTRACT

Dispirotetradecanes of the formula I

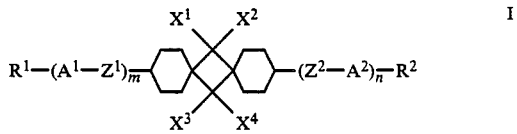

wherein $R^1$ and $R^2$ are each independently of each other alkyl containing 1 to 12 carbon atoms wherein one or more non-adjacent $CH_2$ groups may also be replaced by —O—, —CO—, —CO—O—, —O—CO—, —O—COO— and/or —CH=CH— (trans), one of the radicals $R^1$ and $R^2$ also being H, F, Cl, Br, I, CN, $NO_2$, NCS, $A^1$ and $A^2$ are each independently of each other trans-1,4-cyclohexylene wherein one or two non-adjacent $CH_2$ groups may be replaced by —O— and/or —S—, or 1,4-phenylene wherein one or more CH groups may also be replaced by N, with it also being possible optionally for $A^1$ and $A^2$ to be substituted laterally or axially by F, Cl, CN, $CH_3$, $Z^1$ and $Z^2$ are each independently of each other —C—O—, —O—CO—, —$CH_2CH_2$—, —$CH_2O$—, —$OCH_2$— or a single bond, m and n are each 0, 1 or 2, (m+n) 0, 1 or 2, $X^1$, $X^2$, $X^3$ and $X^4$ are each independently of each other H, F, Cl or CN, and one or both of the groups $CX^1X^2$ and $CX^3X^4$ may also be C=O, may be used as components of liquid-crystalline phases.

12 Claims, No Drawings

DISPIROTETRADECANES

The invention relates to dispirotetradecanes of the formula I

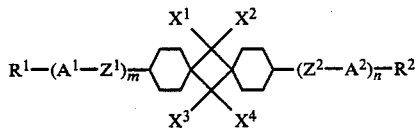

wherein $R^1$ and $R^2$ are each independently of the other alkyl containing 1 to 12 carbon atoms wherein one or more non-adjacent $CH_2$ groups may also be replaced by —O—, —CO—, —CO—O—, —O—CO—, —O—COO— and/or —CH=CH— (trans), one of the radicals $R^1$ and $R^2$ also being H, F, Cl, Br, I, CN, $NO_2$, NCS, $A^1$ and $A^2$ are each independently of the other trans1,4-cyclohexylene wherein one or two nonadjacent $CH_2$ groups may be replaced by —O— and/or —S—, or 1,4-phenylene wherein one or more CH groups may also be replaced by N, with it also being possible optionally for $A^1$ and $A^2$ to be substituted laterally or axially by F, Cl, CN, $CH_3$, $Z^1$ and $Z^2$ are each independently of the other —CO—O—, —O—CO—, —$CH_2CH_2$—, —$CH_2O$—, —$OCH_2$— or a single bond, m and n are each 0, 1 or 2, (m+n) 0, 1 or 2, $N^1$, $X^2$, $X^3$ and $X^4$ are each independently of the other H, F, Cl or Cn, and one or both of the groups $CX^1X^2$ and $CX^3X^4$ may also be C=O, with the proviso that (m+n) is 1 or 2 if both groups $CX^1X^2$ and $CX^3X^4$ are C=O.

For the sake of simplicity, in what follows Cy is a 1,4-cyclohexylene group, Dio is a 1,3-dioxane-2,5-diyl group, Dit is a 1,3-dithiane-2,5-diyl group and Phe is a 1,4-phenylene group.

Similar compounds are known, for example, from German Offenlegungsschrift No. 3,426,035 and German Offenlegungsschrift No. 3,407,013. However, in contrast to the present compounds, the compounds specified there always contain cyclohexane rings linked via a single bond while the novel compounds always have the dispirotetradecane structure.

The compounds of the formula I can be used like similar compounds as components of liquid-crystalline phases, in particular for displays which are based on the principle of the twisted cell (TN displays), the guest-host effect, the aligned phase deformation effect, the dynamic scattering effect or the SSFLC principle.

The invention was based on the object of finding novel stable liquid-crysalline or mesogenic compounds which are suitable as components of liquid-crystalline phases.

It has now been found that the compounds of the formula I are eminently suitable as components of liquid-crystalline phases. In particular, they are suitable for wide-range mixtures with particularly low optical anisotropy.

In addition, the provision of the compounds of the formula I substantially widens, quite generally, the range of liquid-crystalline substances which are suitable for producing liquid-crystalline mixtures from various application points of view.

The compounds of the formula I have a wide field of application. Depending on the choice of substituents, these compounds can act as base materials of which liquid-crystalline phases are predominantly composed; however, compounds of the formula I may also be added to liquid-crystalline base materials from other compound categories in order, for example, to optimize the dielectric and/or optical anisotropy or other parameters of such a dielectric. The compounds of formula I for furthermore suitable as intermediate products for preparing other substances which can be used as constituents of liquid-crystalline phases. In the pure state, the compounds of the formula I are colorless and form liquid-crystalline mesophases in a temperature range which is favorably situated for electrooptical use. They are very stable chemically, thermally and towards light.

The subject of the invention is therefore formed by the compounds of the formula I and also by a method for producing them, wherein suitably substituted cyclohexanecarboxylic acid halides are converted into the ketenes by dehydrohalogenation and the latter are dimerized to the dispirotetradecanedione system, or wherein one or both C=O groups in a compound which otherwise corresponds to the formula I but contains two C=O groups in the 7,14 position are treated with a reducing agent, or wherein, to produce esters of the formula I (wherein $R^1$ and/or $R^2$ is an alkyl group wherein one or more $CH_2$ groups are replaced by —O—CO— groups and/or —CO—O— groups and/or wherein $Z^1$ and/or $Z^2$ is —CO—O— or —O—CO—), a corresponding carboxylic acid or one of its reactive derivatives is reacted with a corresponding alcohol or one of its reactive derivatives, or wherein, to produce 1,3-dioxane derivatives or 1,4-dithiane derivatives of the formula I (wherein $A^1$ and/or $A^2$ is 1,3-dioxane-2,5-diyl or 1,3-dithianne-2,5-diyl), a corresponding aldehyde is reacted with a corresponding diol or dithiol, or wherein to produce ethers of the formula I (wherein $R^1$ and/or $R^2$ is an alkyl group wherein one or more $CH_2$ groups are replaced by O atoms and/or $Z^1$ and/or $Z^2$ is an —$OCH_2$— or —$CH_2O$— group), a corresponding hydroxyl compound is esterified, or wherein, to produce nitrites of the formula I (wherein $X^1$, $X^2$, $X^3$ and/or $X^4$ is CN), the corresponding chlorine or bromine compounds are reacted with a cyanide.

Furthermore, the subject of the invention is the use of compounds of the formula I

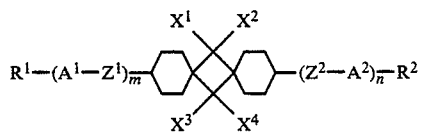

wherein $R^1$ and $R^2$ are each independently of the other alkyl containing 1 to 12 carbon atoms wherein one or more non-adjacent $CH_2$ groups may also be replaced by —O—, —CO—, —CO—O—, —O—CO—, —O—COO— and/or —CH=CH— (trans), one of the radicals $R^1$ and $R^2$ also being H, F, Cl, Br, I, CN, $NO_2$, NCS, $A^1$ and $A^2$ are each independently of the other trans1,4-cyclohexylene wherein one or two nonadjacent $CH_2$ groups may be replaced by —O— and/or —S—, or 1,4-phenylene wherein one or more CH groups may also be replaced by N, with it also being possible optionally for $A^1$ and $A^2$ to be substituted laterally or axially by F, Cl, CN, $CH_3$, $Z^1$ and $Z^2$ are each independently of the other —CO—O—, —O—CO—, —$CH_2CH_2$—, —$CH_2O$—, —$OCH_2$— or a single bond, m and n are each 0, 1 or 2, (m+n) 0, 1 or 2, $X^1$, $X^2$, $X^3$ and $X^4$ are each independently of the other H, F, Cl or CN, and one or both of the groups $CX^1X^2$ and $CX^3X^4$ may also be C=O, as components of liquid-crystalline phases with a particularly low optical anisotropy, preferably with $\Delta n \leq 0.09$, in particular $\Delta n \leq 0.08$. The subject of the invention is also formed by liquid-crystalline phases containing at least two liquid-crystalline components, wherein at least one component of the phase is a compound containing the structural element

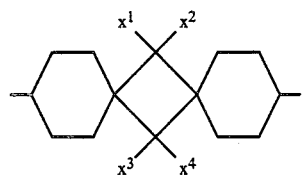

wherein $X^1$, $X^2$, $X^3$ and $X^4$ are each independently of the other H, F, Cl or CN and one or both of the groups $CX^1X^2$ and $CX^3X^4$ may also be C=O. The subject of the invention is furthermore formed by liquid-crystalline phases with a content of at least one compound of the formula I and also liquid-crystalline display elements, in particular electrooptical display elements which contain such phases.

Above and below, $R^1$, $R^2$, $A^1$, $A^2$, $Z^1$, $Z^2$, $X^1$, $X^2$, $X^3$, $X^4$, m and n have the specified meaning unless anything else is expressly noted.

The compounds of the formula I include compounds of the partial formulae Ia to Id:

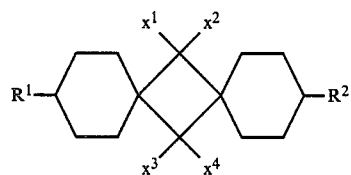
Ia

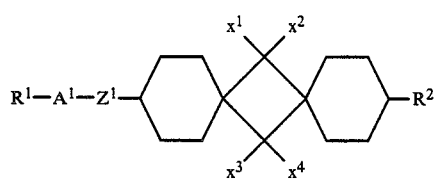
Ib

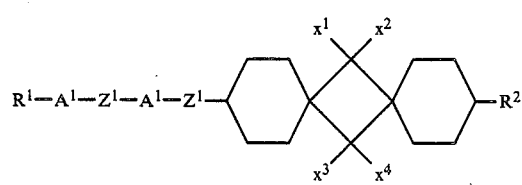
Ic

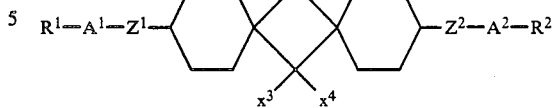
Id

Of these, those of the partial formulae Ia and Id are particularly preferred.

The structural element

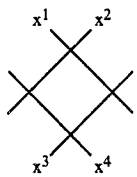

is preferably

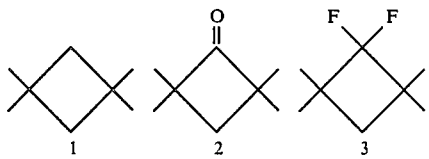
1  2  3

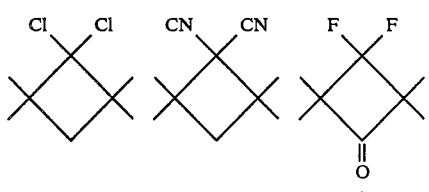
4  5  6

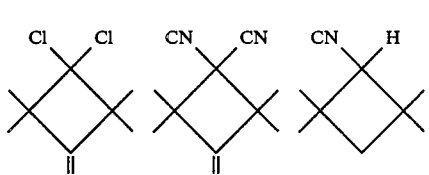
7  8  9

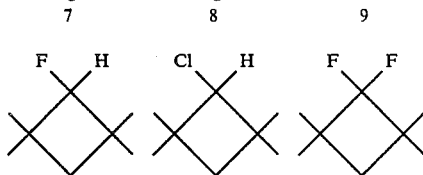
10  11  12

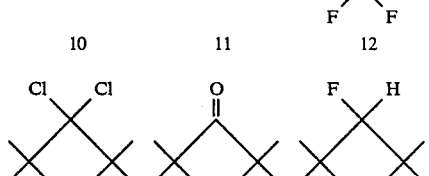

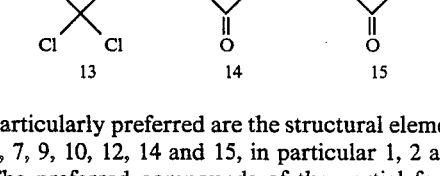
13  14  15

Particularly preferred are the structural elements 1, 2, 3, 5, 7, 9, 10, 12, 14 and 15, in particular 1, 2 and 3.

The preferred compounds of the partial formula Ia include those of the partial formulae Iaa to Iag:

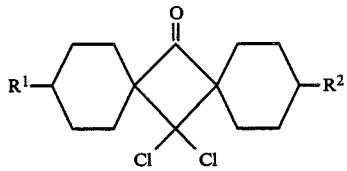 Iaa

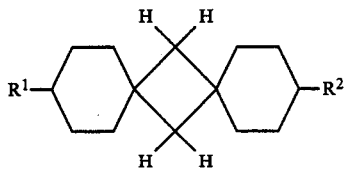 Iab

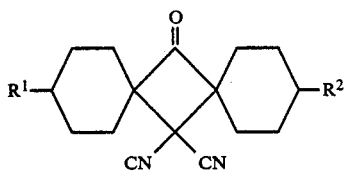 Iac

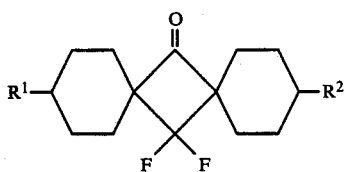 Iad

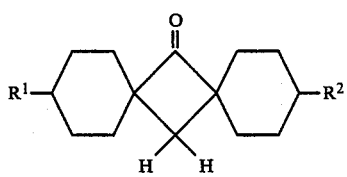 Iae

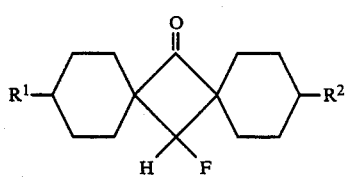 Iaf

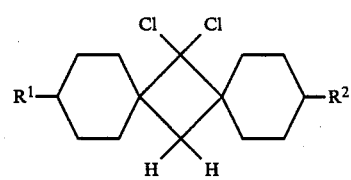 Iag

Of these, those of the partial formulae Iab, Iae and Iag are particularly preferred.

The preferred compounds of the partial formula Ib include those of the partial formulae Iba to Ibd:

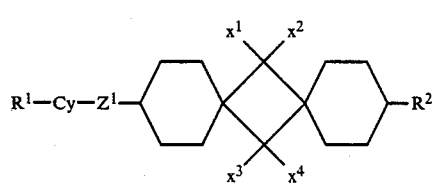 Iba

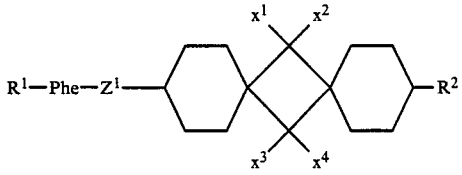 Ibb

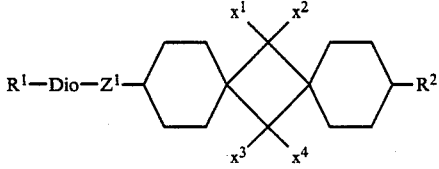 Ibc

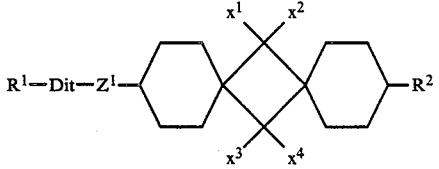 Ibd

In the partial formulae Iba to Ibd, $Z^1$ is primarily a single bond and secondarily —CO—O— or —O—CO—, $X^1$-$X^4$ are preferably H and furthermore also Cl, F or CN, and one or both of the groups $CX^1X^2$ and $CX^3X^4$ may also be C=O.

Of these, those of the partial formula Iba are particularly preferred.

The preferred compounds of the partial formula Ic include those of the partial formulae Ica to Icd:

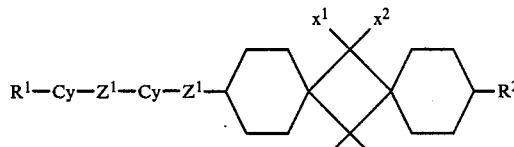 Ica

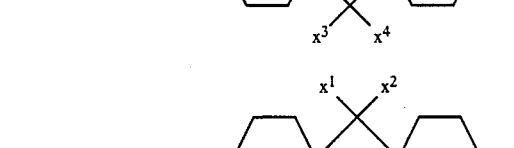 Icb

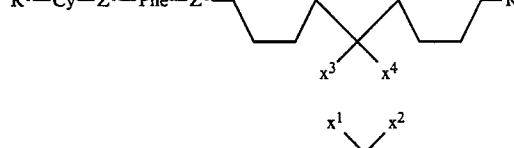 Icc

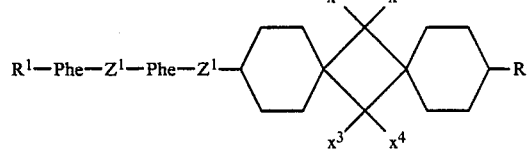 Icd

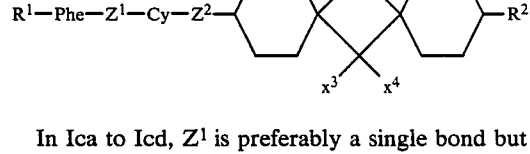

In Ica to Icd, $Z^1$ is preferably a single bond but furthermore also —CO—O— or —O—CO—, $X^1$-$X^4$ are preferably H, but furthermore also Cl, F or CN, and one or both of the groups $CX^1X^2$ and $CX^3X^4$ may also be C=O.

Of these, those of the partial formulae Ica and Icd are particularly preferred.

The preferred compounds of the partial formula Id include those of the partial formulae Ida to Ide:

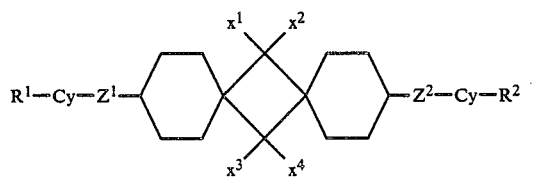
Ida

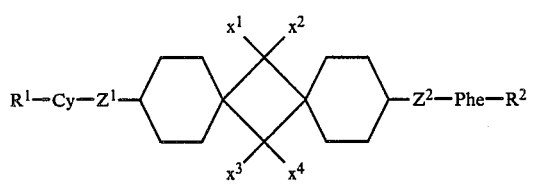
Idb

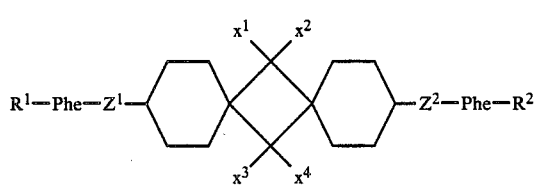
Idc

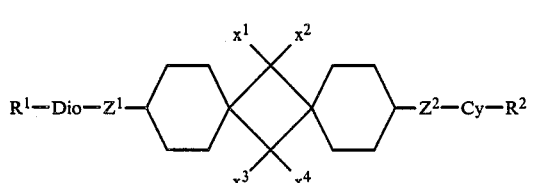
Idd

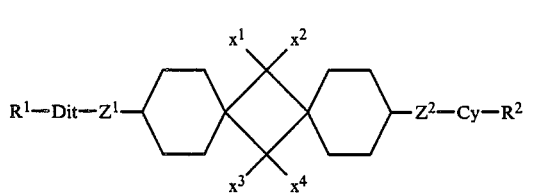
Ide

In the partial formulae Ida to Ide, $Z^1$ and/or $Z^2$ are primarily single bonds and secondarily —CO—O— or —O—CO—; $X^1$-$X^4$ are preferably H, but furthermore also Cl, CN or F; one or both of the groups $CX^1X^2$ and $CX^3X^4$ may also be C=O.

Of these, those of the partial formula Ida are particularly preferred.

In the compounds of the formulae above and below, $R^1$ and $R^2$ are preferably alkyl, —O—alkyl, —O—CO—alkyl or —COO—alkyl, in particularly alkyl, and if linked to Phe, also CN, F, NCS, $NO_2$.

$A^1$ and $A^2$ are preferably Cy or Phe.

$Z^1$ and $Z^2$ are preferably single bonds, furthermore preferably also —CO—O—, —O—CO—, —$CH_2$O—, —O$CH_2$— or —$CH_2CH_2$— groups.

$X^1$-$X^4$ are preferably H, furthermore F, Cl or CN.

Furthermore, one or both of the groups $CX^1X^2$ and $CX^3X^4$ may also be a C=O group.

If $CX^1X^2$ and $CX^3X^4$ are C=O, (m+n) is 1 or 2. m and n are preferably 0 or 1.

The alkyl radicals in the groups $R^1$ and/or $R^2$ may be straight-chain or branched. Preferably, they are straight-chain, contain 1, 2, 3, 4, 5, 6, 7, 8, 9 or 10 carbon atoms and therefore denote preferably methyl, ethyl, propyl, butyl, pentyl, hexyl, heptyl, octyl, nonyl or decyl, furthermore undecyl or dodecyl.

If $R^1$ and/or $R^2$ are alkyl radicals in which preferably one ("alkoxy" or "oxaalkyl") or two ("alkoxy-alkoxy" or "dioxaalkyl") $CH_2$ groups are replaced by O atoms, they may be straight-chain or branched. Preferably, they are straight-chain, contain 2, 3, 4, 5, 6 or 7 carbon atoms and therefore are preferably ethoxy, propoxy, butoxy, pentoxy, hexoxy, heptoxy, 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, furthermore methoxy, octoxy, nonoxy, decoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4- or 3,5-dioxahexyl, 1,3-, 1,4-, 1,5-, 1,6-, 2,4-, 2,5-, 2,6-, 3,5-, 3,6- or 4,6-dioxaheptyl.

Compounds of the formula I and also of the partial formulae above and below with branched wing groups $R^1$ or $R^2$ may occasionally be of important because of a better solubility in the usual liquid-crystalline base materials, in particular, however, as chiral dopants if they are optically active. Such compounds are furthermore suitable as components of ferroelectric liquid-crystalline phases. Branched groups of this type contain as a rule not more than one chain branching. Preferred branched radicals $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 2-octyloxy.

The compounds of the formula I are prepared by methods known per se such as are described in the literature (for example, in the standard works such as Houben Weyl, Methoden der organischen Chemie (Methods of Organic Chemistry), Georg-Thieme-Verlag, Stuttgart) and in particular, under reaction conditions which are known and suitable for the reactions mentioned. At the same time, use may also be made of variants which are known per se but are not mentioned here.

Those skilled in the art may also draw on synthesis methods from the prior art through routine methods (for example, Japanese Pat. No. 59-152343 relating to the dispiro(5.1.5.1)tetradecane-7,14-diones; the German Offenlegungsschriften Nos. 2,344,732, 24,540,088, 2,429,093, 2,502,304, 2,636,684, 2,701,591 and 2,752,975 relating to compounds containing 1,4-cyclohexylene and 1,4-phenylene groups; German Offenlegungsschriften Nos. 2,944,905 and 3,227,916 relating to compounds containing 1,3-dioxane-2,5-diyl groups; and for example, German Offenlegungsschrift No. 3,201,721 relating to compounds containing —$CH_2CH_2$— bridging links).

The starting materials may, if desired, also be formed in situ in a manner such that they are not isolated from the reaction mixture but are immediately converted into the compounds of the formula I.

Thus, the compounds of the formula I can be prepared by dehydrohalogenating substituted cyclohexanecarboxylic acid halides in an inert solvent such as, for example, benzene, toluene, by means of a base while heating, and dimerizing the ketene produced to form dispirotetradecanedione.

Furthermore, the compounds of the formula I may be prepared by treating one or both keto groups in appropriate 3,11-disubstituted dispirotetradecane-7,14-diones, which can be prepared, for example, by ketene dimerization, with a reducing agent. To introduce halogen substituents, the dispirotetradecanedione is preferably reacted in an inert solvent such as, for example, carbon tetrachloride, chloroform, ether, with an inorganic acid halide, for example phosphorus pentachloride, phosphorus pentabromide, at temperatures of 0°–100°, preferably at room temperature.

Compounds of the formula I may also be prepared by reducing a compound which otherwise corresponds to the formula I, but contains instead of H atoms one or more reducible groups and/or C—C bonds.

As reducible groups, carbonyl groups are preferably suitable, in particular keto groups, furthermore for example, free or esterified hydroxy groups or aromatically bonded halogen atoms. Preferable starting substances for the reduction correspond to the formula 1, but may contain, instead of a cyclohexane ring, a cyclohexene ring or cyclohexanone ring and/or, instead of a —CH$_2$CH$_2$— group, a —CH=CH— group and/or, instead of a —CH$_2$— group, a —CO— group and/or, instead of an H atom, a free or a functionally modified OH group (for example in the form of its p-toluenesulfonate). The carbonyl groups of the dispiro compound in the 7- and 14-position may also be reduced by usual reduction methods.

The reduction may, for example, take place by catalytic hydrogenation at temperatures between about 0° and about 200° and also pressures between about 1 and 200 bar in an inert solvent, for example an alcohol such as methanol, ethanol or isopropanol, an ether such as tetrahydrofuran (THF) or dioxane, an ester such as ethyl acetate, a carboxylic acid such as acetic acid or a hydrocarbon such as cyclohexane. Suitable as catalysts are expediently noble metals such as Pt or Pd which may be used in the form of oxides (for example PtO$_2$, PdO), on a carrier (for example Pd on charcoal, calcium carbonate or strontium carbonate) or in a finely divided form.

Ketones can also be reduced to the corresponding compounds of the formula I which contain alkyl groups and/or —CH$_2$CH$_2$ bridges by the methods of Clemmensen (with zinc, amalgamated zinc or zinc and hydrochloric acid, expediently in aqueous-alcoholic solution or in a heterogeneous phase containing water/toluene at temperatures between about 80° and 120° C.) or of Wolff-Kishner (with hydrazine, expediently in the presence of alkali such as KOH or NaOH in a high-boiling solvent such as diethylene glycol or triethylene glycol at temperatures between about 100° and 200° C.). With the sensitivity of the four-ring diketone, these methods may not be successful in certain cases (depending on the substitution). In such cases, more gentle methods must be used (reduction of the dihalides with sodium or of the thioketones or thioketals with Raney nickel).

Furthermore, reduction with complex hydrides is possible. For example, arylsulfonyloxy groups may be removed reductively with LiAlH$_4$, and in particular ptoluenesulfonyloxymethyl groups can be reduced to methyl groups, expediently in an inert solvent such as diethyl ether or THF at temperatures between about 0° and 100° C. Double bonds may also be hydrogenated (even in the presence of CN groups!) with NaBH$_4$ or tributyltin hydride in methanol.

Esters of the formula I ($R^1$ and/or $R^2$=alkyl, wherein one or more CH$_2$ groups are replaced by —O—CO— and/or —CO—O— groups and/or $Z^1$ and $Z^2$=—CO—O— or —O—CO—) can also be obtained by esterification of corresponding carboxylic acids (or their reactive derivatives) with alcohols or phenols (or their reactive derivatives).

Acid halides, in particular the chlorides and bromides, furthermore the anhydrides, azides or esters, in particular alkyl esters containing 1-4 carbon atoms in the alkyl group are suitable as reactive derivatives of the carboxylic acids mentioned.

In particular, the corresponding metal alcoholates or phenolates, preferably of an alkali metal such as Na or K, are suitable as reactive derivatives of the alcohols or phenols mentioned.

the esterification is advantageously carried out in the presence of an inert solvent. In particular ethers such as diethyl ether, di-n-butyl ether, THF, dioxane or anisole, ketones such as acetone, butanone or cyclohexanone, amides such as DMF or phosphoric acid hexamethyltriamide, hydrocarbons such as benzene, toluene or xylene, halogenated hydrocarbons such as carbon tetrachloride or tetrachloroethylene and sulfoxides such as dimethylsulfoxide or sulfolane are well suited. Solvents which are not miscible with water may at the same time advantageously be used for azeotropically distilling off the water formed during the esterification. Occasionally, an excess of an organic base, for example pyridine, quinoline or triethylamine, may also be used as a solvent for the esterification. The esterification can also be carried out in the absence of a solvent, for example by simply heating the components in the presence of sodium acetate. The reaction temperature is usually between −50° and +250° C., preferably between −20° and +80°. At these temperatures, the esterification reactions are as a rule complete after 15 minutes to 48 hours.

In detail, the reaction conditions for the esterification depend substantially on the nature of the starting substances used. Thus, a free carboxylic acid is reacted with a free alcohol or phenol as a rule in the presence of a strong acid, for example a mineral acid such as hydrochloric acid or sulfuric acid. A preferred mode of reaction is the reaction of an acid anhydride or, in particular, an acid chloride with an alcohol, preferably in a basic medium, in particular alkali metal hydroxides, such as sodium or potassium hydroxide, alkali metal carbonates or hydrogencarbonates, such as sodium carbonate, sodium hydrogencarbonate, potassium carbonate or potassium hydrogencarbonate, alkali metal acetates such as sodium or potassium acetate, alkaline earth metal hydroxides such as calcium hydroxide or organic bases such as triethylamine, pyridine, lutidine, collidine or quinoline being of importance as bases. A further preferred embodiment of the esterification consists in converting the alcohol or the phenol first into the sodium or potassium alcoholate or phenolate, for example by treatment with ethanolic sodium or potassium hydroxide, isolating this and suspending it together with sodium hydrogencarbonate or potassium carbonate in acetone or diethyl ether with stirring, and mixing this suspension with a solution of the acid chloride or anhydride in diethyl ether, acetone or DMF, expediently at temperatures between about −25° and +20°.

Dioxane derivatives or dithiane derivatives of the formula I (wherein one of the groups $A^1$ and/or $A^2$ is a 1,3-dioxane-2,5-diyl group or a 1,3-dithiane-2,5-diyl group) are expediently prepared by reaction of a corresponding aldehyde with a corresponding 1,3-diol or a corresponding 1,3-dithiol (or one of its reactive derivatives), preferably in the presence of an inert solvent such as benzene or toluene and/or a catalyst, for example a strong acid such as sulfuric acid, benzene- or p-toluenesulfonic acid, at temperatures between about 20° and about 150°, preferably between 80° and 120° C. Acetals are primarily suitable as reactive derivatives of the starting substances.

The aldehydes, 1,3-diols and 1,3-dithiols mentioned and also their reactive derivatives are in some cases known, and in some cases they can be prepared without difficulty by standard methods of organic chemistry from compounds known from the literature. For example, the aldehydes can be obtained by oxidizing corresponding alcohols or by reducing corresponding carboxylic acids or their derivatives, the diols by reducing corresponding diesters, and also the dithiols by reacting corresponding dihalides with NaSH.

Ethers of the formula I (wherein $R^1$ and/or $R^1$ is an alkyl group, wherein one or more $CH_2$ groups are replaced by 0 atoms, and/or wherein $Z^1$ and/or $Z^2$ is an $-OCH_2-$ or a $-CH_2O$ group) can be obtained by etherifying corresponding hydroxyl compounds, preferably corresponding phenols, the hydroxyl compound expediently being converted first into a corresponding metal derivative, for example by treatment with NaH, $NaNH_2$, NaOH, KOH, $Na_2CO_3$ or $K_2CO_3$ to the corresponding alkali metal alcoholate or alkali metal phenolate. This may then be reacted with the corresponding alkyl halide, sulfonate or dialkyl sulfonate, expediently in an inert solvent such as acetone, 1,2-dimethoxyethane, DMF or dimethyl sulfoxide or also in an excess of aqueous or aqueous-alcoholic NaOH or KOH at temperatures between about 20° and 100°.

To prepare nitriles of the formula I (wherein $X^1$ and/or $X^2$ and/or $X^3$ and/or $X^4$ is CN), corresponding chlorine or bromine compounds of the formula I may be reacted with a cyanide, expediently with a metal cyanide such as NaCN, KCN or $Cu_2(CN)_2$, for example in the presence of pyridine in an inert solvent such as DMF or N-methylpyrrolidone at temperatures between 20° and 200°.

The novel liquid-crystalline phases consist of 2 to 15, preferably 3 to 15 components, including at least one compound of the formula I. The other constituents are preferably selected from the nematic or nematogenic substances, in particular the known substances, from the categories of the azoxybenzenes, benzylideneanilines, biphenyls, terphenyls, phenylbenzoates or cyclohexylbenzoates, phenyl or cyclohexyl esters of cyclohexanecarboxylic acid, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenyl- or cyclohexylpyrimidines, phenyl- or cyclohexyldioxanes, phenyl- or cyclohexyl-1,3-dithianes, 1-phenyl-2-cyclohexylethanes, optionally halogenated stilbenes, benzyl phenyl ether, tolanes and substituted cinnamic acids.

The most important compounds suitable as constituents of such liquid-crystalline phases may be characterized by the formula II, $$R'-L-G-E-R''$$ II wherein L and E are each a carbo- or heterocyclic ring system from the group formed from 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted napthalene, di- and tetrahydronaphthalene, quinazoline and tetrahydroquinazoline, G is

| | |
|---|---|
| $-CH=CH-$ | $-N(O)=N-$ |
| $-CH=CY-$ | $-CH=N(O)-$ |
| $-C\equiv C-$ | $-CH_2-CH_2-$ |
| $-CO-O-$ | $-CH_2-O-$ |
| $-CO-S-$ | $-CH_2-S-$ |
| $-CH=N-$ | $-COO-Phe-COO-$ | or a single C—C bond, Y is halogen, preferably chlorine, or CN, and R' and R'' are alkyl, alkoxy, alkanoyloxy or alkoxycarbonyloxy containing up to 18, preferably up to 8 carbon atoms, or one of these radicals is also CN, NC, $NO_2$, $CH_3$, F, Cl or Br.

In most of these compounds, R' and R'' are different from each other, one of these radicals mostly being an alkyl or alkoxy group. However, other variants of the substituents envisaged are also common. Many such substances or also mixtures thereof are obtainable commercially. All these substances can be prepared by methods known from the literature.

The novel phases contain about 0.1 to 99, preferably 10 to 95%, of one or more of the compounds of the formula I.

Furthermore, novel dielectrics containing 0.1 to 40, preferably 0.5 to 30%, of one or more compounds of the formula I are preferred.

The preparation of the novel dielectrics takes places in a manner which is known per se. As a rule, the components are dissolved in each other, expediently at elevated temperature.

The liquid-crystalline dielectrics according to the invention may be modified by suitable additives so that they can be used in all the types of liquid-crystalline display elements which have become known hitherto.

Such additives are known to those skilled in the art and are described comprehensively in the literature. For example, supporting electrolytes, preferably ethyldimethyldodecylammonium 4-hexyloxybenzoate, tetrabutylammonium tetraphenylboranate or complex salts of crown ethers (cf., for example, I. Haller et al., Mol. Cryst. Liq. Cryst., vol. 24, pages 249–258 (1973)) may be added to improve the conductivity, dichroic dyestuffs to produce colored guest-host systems or substances to modofy the dielectric anisotropy, the viscosity and/or the orientation of the nematic phases. Such substances are, for example, described in the German Offenlegungsschriften Nos. 2,209,127, 2,240,854, 2,321,632, 2,338,281, 2,450,088, 2,637,430, 2,853,728 and 2,902,177.

The examples which follow are intended to explain the invention without restricting it. m.p.=melting point, c.p.=clearing point. Percentage data above and below are percentages by weight; all temperatures are specified in degrees Celsius. K denotes crystalline state, N denotes nematic and I denotes isotropic state. The numbers between K, N and I represent the transition temperatures.

EXAMPLE 1

3.0 g of triethylamine in 100 ml of benzene are added dropwise with stirring to a mixture of 5.4 g of trans-4-(trans-4-n-propylcyclohexyl)cyclohexanecarboxylic acid chloride and 50 ml of benzene, and stirring is then carried out for 8–24 h under reflux. After separating off the triethylammonium chloride, the filtrate is washed until neutral and the organic phase worked up. After recrystallization, 3,11-bis(trans-4-n-propylcyclohexyl)-dispiro[5.1.5.1]tetradecane-7,14-dione is obtained and after chromatographic separation of the isomers, the pure trans-dispiro compound is obtained with m.p. of 290°.

The following are prepared analogously:

3,11-bis(trans-4-methylcyclohexyl)dispiro[5.1.5.1]tetradecane-7,14-dione
3,11-bis(trans-4-ethylcyclohexyl)dispiro[5.1.5.1]tetradecane-7,14-dione
3,11-bis(trans-4-butylcyclohexyl)dispiro[5.1.5.1]tetradecane-7,14-dione
3,11-bis(trans-4-pentylcyclohexyl)dispiro[5.1.5.1]tetradecane-7,14-dione
3,11-bis(trans-4-hexylcyclohexyl)dispiro[5.1.5.1]tetradecane-7,14-dione
3,11-bis(trans-4-heptylcyclohexyl)dispiro[5.1.5.1]tetradecane-7,14-dione
3,11-bis(trans-4-octylcyclohexyl)dispiro[5.1.5.1]tetradecane-7,14-dione
3,11-bis(trans-4-nonylcyclohexyl)dispiro[5.1.5.1]tetradecane-7,14-dione
3,11-bis(trans-4-decylcyclohexyl)dispiro[5.1.5.1]tetradecane-7,14-dione
3,11-bis(trans-4-methoxycyclohexyl)dispiro[5.1.5.1]tetradecane-7,14-dione
3,11-bis(trans-4-ethoxycyclohexyl)dispiro[5.1.5.1]tetradecane-7,14-dione
3,11-bis(trans-4-propoxycyclohexyl)dispiro[5.1.5.1]tetradecane-7,14-dione
3,11-bis(trans-4-butoxycyclohexyl)dispiro[5.1.5.1]tetradecane-7,14-dione
3,11-bis(trans-4-pentoxycyclohexyl)dispiro[5.1.5.1]tetradecane-7,14-dione
3,11-bis(trans-4-hexoxycyclohexyl)dispiro[5.1.5.1]tetradecane-7,14-dione
3,11-bis(trans-4-heptoxycyclohexyl)dispiro[5.1.5.1]tetradecane-7,14-dione
3,11-bis(trans-4-octoxycyclohexyl)dispiro[5.1.5.1]tetradecane-7,14-dione
3,11-bis(trans-4-nonoxycyclohexyl)dispiro[5.1.5.1]tetradecane-7,14-dione
3,11-bis(trans-4-decoxycyclohexyl)dispiro[5.1.5.1]tetradecane-7,14-dione
3,11-bis(4-methylphenyl)dispiro[5.1.5.1]tetradecane-7,14-dione
3,11-bis(4-ethylphenyl)dispiro[5.1.5.1]tetradecane-7,14-dione
3,11-bis(4-propylphenyl)dispiro[5.1.5.1]tetradecane-7,14-dione
3,11-bis(4-butylphenyl)dispiro[5.1.5.1]tetradecane-7,14-dione
3,11-bis(4-pentylphenyl)dispiro[5.1.5.1]tetradecane-7,14-dione
3,11-bis(4-hexylphenyl)dispiro[5.1.5.1]tetradecane-7,14-dione
3,11-bis(4-heptylphenyl)dispiro[5.1.5.1]tetradecane-7,14-dione
3,11-bis(4-octylphenyl)dispiro[5.1.5.1]tetradecane-7,14-dione
3,11-bis(4-nonylphenyl)dispiro[5.1.5.1]tetradecane-7,14-dione
3,11-bis(4-decylphenyl)dispiro[5.1.5.1]tetradecane-7,14-dione
3,11-bis(4-methoxyphenyl)dispiro[5.1.5.1]tetradecnae-7,14-dione
3,11-bis(4-ethoxyphenyl)dispiro[5.1.5.1]tetradecane-7,14-dione
3,11-bis(4-propoxyphenyl)dispiro[5.1.5.1]tetradecane-7,14-dione
3,11-bis(4-butoxyphenyl)dispiro[5.1.5.1]tetradecane-7,14-dione
3,11-bis(4-pentoxyphenyl)dispiro[5.1.5.1]tetradecane-7,14-dione
3,11-bis(4-hexoxyphenyl)dispiro[5.1.5.1]tetradecane-7,14-dione
3,11-bis(4-heptoxyphenyl)dispiro[5.1.5.1]tetradecane-7,14-dione
3,11-bis(4-octoxyphenyl)dispiro[5.1.5.1]tetradecane-7,14-dione
3,11-bis(4-nonoxyphenyl)dispiro[5.1.5.1]tetradecane-7,14-dione
3,11-bis(4-decoxyphenyl)dispiro[5.1.5.1]tetradecane-7,14-dione
3-(trans-4-methylcyclohexyl)-11-(trans-4-ethylcyclohexyl)-dispiro[5.1.5.1]tetradecane-7,14-dione
3-(trans-4-ethylcyclohexyl)-11-(trans-4-pentylcyclohexyl)-dispiro[5.1.5.1]tetradecane-7,14-dione
3-(trans-4-propylcyclohexyl)-11-(trans-4-ethylcyclohexyl)-dispiro[5.1.5.1]tetradecane-7,14-dione
3-(trans-4-butylcyclohexyl)-11-(trans-4-ethylcyclohexyl)-dispiro[5.1.5.1]tetradecane-7,14-dione
3-(trans-4-hexylcyclohexyl)-11-(trans-4-ethylcyclohexyl)-dispiro[5.1.5.1]tetradecane-7,14-dione
3-(trans-4-ethylcyclohexyl)-11-(trans-4-heptylcyclohexyl)-dispiro[5.1.5.1]tetradecane-7,14-dione
3-(trans-4-octylcyclohexyl)-11-(trans-4-propylcyclohexyl)-dispiro[5.1.5.1]tetradecane-7,14-dione
3-(trans-4-butylcyclohexyl)-11-(trans-4-nonylcyclohexyl)-dispiro[5.1.5.1]tetradecane-7,14-dione
3-(trans-4-decylcyclohexyl)-11-(trans-4-hexylcyclohexyl)-dispiro[5.1.5.1]tetradecane-7,14-dione
3-(trans-4-propylcyclohexyl)-11-(trans-4-pentylcyclohexyl)-dispiro[5.1.5.1]tetradecane-7,14-dione
3-(trans-4-pentylcyclohexyl)-11-(trans-4-heptylcyclohexyl)-dispiro[5.1.5.1]tetradecane-7,14-dione
3-(trans-4-propylcyclohexyl)-11-trans-pentyldispiro[5.1.5.1]tetradecane-7,14-dione
3-(trans-4-propylcyclohexyl)-11-trans-propyldispiro[5.1.5.1]tetradecane-7,14-dione
3-(trans-4-propylcyclohexyl)-11-trans-ethyldispiro[5.1.5.1]tetradecane-7,14-dione
3-(trans-4-propylcyclohexyl)-11-trans-butyldispiro[5.1.5.1]tetradecane-7,14-dione
3-(trans-4-butylcyclohexyl)-11-trans-butyldispiro[5.1.5.1]tetradecane-7,14-dione
3-(trans-4-propylcyclohexyl)-11-trans-hexyldispiro[5.1.5.1]tetradecane-7,14-dione
3-(trans-4-pentylcyclohexyl)-11-trans-pentyldispiro[5.1.5.1]tetradecane-7,14-dione
3-(trans-4-ethylcyclohexyl)-11-trans-pentyldispiro[5.1.5.1]tetradecane-7,14-dione
3-(trans-4-methylcyclohexyl)-11-trans-propyldispiro[5.1.5.1]tetradecane-7,14-dione
3-(trans-4-pentylcyclohexyl)-11-trans-methyldispiro[5.1.5.1]tetradecane-7,14-dione 3-(trans-4-heptylcyclohexyl)-11-trans-heptyldispiro-[5.1.5.1]tetradecane-7,14-dione
3-[trans-4-(p-propylcyclohexyl)cyclohexyl]-11-transpentyldispiro[5.1.5.1]tetradecane-7,14-dione
3-[trans-4-(p-propylcyclohexyl)cyclohexyl]-11-transpropyldispiro[5.1.5.1]tetradecane-7,14-dione
3-[trans-4-(p-propylcyclohexyl)cyclohexyl]-11-transethyldispiro[5.1.5.1]tetradecane-7,14-dione
3-[trans-4-(p-pentylcyclohexyl)cyclohexyl]-11-transpentyldispiro[5.1.5.1]tetradecane-7,14-dione
3-[trans-4-(p-pentylcyclohexyl)cyclohexyl]-11-transpropyldispiro[5.1.5.1]tetradecane-7,14-dione
3-[trans-4-(p-ethylcyclohexyl)cyclohexyl]-11-transbutyldispiro[5.1.5.1]tetradecane-7,14-dione
3-[trans-4-(p-methylcyclohexyl)cyclohexyl]-11-transpropyldispiro[5.1.5.1]tetradecane-7,14-dione
3-[trans-4-(p-pentylcyclohexyl)cyclohexyl]-11-transmethyldispiro[5.1.5.1]tetradecane-7,14-dione
3-[trans-4-(p-heptylcyclohexyl)cyclohexyl]-11-transheptyldispiro[5.1.5.1]tetradecane-7,14-dione.

EXAMPLE 2

1 mmol of 3,11-bis(trans-4-propylcyclohexyl)dispiro-[5.1.5.1]tetradecane-7,14-dione (obtainable according to Example 1) are stirred with 210 mg (1 mmol) of phosphorus pentachloride in 30 ml of carbon tetrachloride for 48 hours at room temperature. After pouring onto ice-water, the organic phase is worked up. After chromatographic purification, 3,11-bis(trans-4-propylcyclohexyl)-14,14-dichlorodispiro[5.1.5.1]tetradecan-7-one is obtained, m.p. 159°, c.p. 266.7°–270.1°.

The following are prepared analogously:
3,11-bis(trans-4-methylcyclohexyl)-14,14-dichlorodispiro-[5.1.5.1]tetradecan-7-one
3,11-bis(trans-4-ethylcyclohexyl)-14,14-dichlorodispiro-[5.1.5.1]tetradecan-7-one
3,11-bis(trans-4-butylcyclohexyl)-14,14-dichlorodispiro-[5.1.5.1]tetradecan-7-one
3,11-bis(trans-4-pentylcyclohexyl)-14,14-dichlorodispiro-[5.1.5.1]tetradecan-7-one
3,11-bis(trans-4-hexylcyclohexyl)-14,14-dichlorodispiro-[5.1.5.1]tetradecan-7-one
3,11-bis(trans-4-heptylcyclohexyl)-14,14-dichlorodispiro-[5.1.5.1]tetradecan-7-one
3,11-bis(trans-4-octylcyclohexyl)-14,14-dichlorodispiro-[5.1.5.1]tetradecan-7-one
3,11-bis(trans-4-nonylcyclohexyl)-14,14-dichlorodispiro-[5.1.5.1]tetradecan-7-one
3,11-bis(trans-4-decylcyclohexyl)-14,14-dichlorodispiro-[5.1.5.1]tetradecan-7-one
3,11-bis(trans-4-methoxycyclohexyl)-14,14-dichlorodispiro-[5.1.5.1]tetradecan-7-one
3,11-bis(trans-4-ethoxycyclohexyl)-14,14-dichlorodispiro-[5.1.5.1]tetradecan-7-one
3,11-bis(trans-4-propoxycyclohexyl)-14,14-dichlorodispiro-[5.1.5.1]tetradecan-7-one
3,11-bis(trans-4-butoxycyclohexyl)-14,14-dichlorodispiro-[5.1.5.1]tetradecan-7-one
3,11-bis(trans-4-pentoxycyclohexyl)-14,14-dichlorodispiro-[5.1.5.1]tetradecan-7-one
3,11-bis(trans-4-hexoxycyclohexyl)-14,14-dichlorodispiro-[5.1.5.1]tetradecan-7-one
3,11-bis(trans-4-heptoxycyclohexyl)-14,14-dichlorodispiro-[5.1.5.1]tetradecan-7-one
3,11-bis(trans-4-octoxycyclohexyl)-14,14-dichlorodispiro-[5.1.5.1]tetradecan-7-one
3,11-bis(trans-4-nonoxycyclohexyl)-14,14-dichlorodispiro-[5.1.5.1]tetradecan-7-one
3,11-bis(trans-4-decoxycyclohexyl)-14,14-dichlorodispiro-[5.1.5.1]tetradecan-7-one
3,11-bis(4-methylphenyl)-14,14-dichlorodispiro[5.1.5.1]-tetradecan-7-one
3,11-bis(4-ethylphenyl)-14,14-dichlorodispiro[5.1.5.1]-tetradecan-7-one
3,11-bis(4-propylphenyl)-14,14-dichlorodispiro[5.1.5.1]-tetradecan-7-one
3,11-bis(4-butylphenyl)-14,14-dichlorodispiro[5.1.5.1]-tetradecan-7-one
3,11-bis(4-pentylphenyl)-14,14-dichlorodispiro[5.1.5.1]-tetradecan-7-one
3,11-bis(4-hexylphenyl)-14,14-dichlorodispiro[5.1.5.1]-tetradecan-7-one
3,11-bis(4-heptylphenyl)-14,14-dichlorodispiro[5.1.5.1]-tetradecan-7-one
3,11-bis(4-octylphenyl)-14,14-dichlorodispiro[5.1.5.1]-tetradecan-7-one
3,11-bis(4-nonylphenyl)-14,14-dichlorodispiro[5.1.5.1]-tetradecan-7-one
3,11-bis(4-decylphenyl)-14,14-dichlorodispiro[5.1.5.1]-tetradecan-7-one
3,11-bis(4-methoxyphenyl)-14,14-dichlorodispiro[5.1.5.1]-tetradecan-7-one
3,11-bis(4-ethoxyphenyl)-14,14-dichlorodispiro[5.1.5.1]-tetradecan-7-one
3,11-bis(4-propoxyphenyl)-14,14-dichlorodispiro[5.1.5.1]-tetradecan-7-one
3,11-bis(4-butoxyphenyl)-14,14-dichlorodispiro[5.1.5.1]-tetradecan-7-one
3,11-bis(4-pentoxyphenyl)-14,14-dichlorodispiro[5.1.5.1]-tetradecan-7-one
3,11-bis(4-hexoxyphenyl)-14,14-dichlorodispiro[5.1.5.1]-tetradecan-7-one
3,11-bis(4-heptoxyphenyl)-14,14-dichlorodispiro[5.1.5.1]-tetradecan-7-one
3,11-bis(4-octoxyphenyl)-14,14-dichlorodispiro[5.1.5.1]-tetradecan-7-one
3,11-bis(4-nonoxyphenyl)-14,14-dichlorodispiro[5.1.5.1]-tetradecan-7-one
3,11-bis(4-decoxyphenyl)-14,14-dichlorodispiro[5.1.5.1]-tetradecan-7-one
3-(trans-4-methylcyclohexyl)-11-(trans-4-ethylcyclohexyl)-14,14-dichlorodispiro[5.1.5.1]tetradecan-7-one
3-(trans-4-ethylcyclohexyl)-11-(trans-4-pentylcyclohexyl)-14,14-dichlorodispiro[5.1.5.1]tetradecan-7-one
3-(trans-4-propylcyclohexyl)-11-(trans-4-ethylcyclohexyl)-14,14-dichlorodispiro[5.1.5.1]tetradecan-7-one
3-(trans-4-butylcyclohexyl)-11-(trans-4-ethylcyclohexyl)-14,14-dichlorodispiro[5.1.5.1]tetradecan-7-one
3-(trans-4-hexylcyclohexyl)-11-(trans-4-ethylcyclohexyl)-14,14-dichlorodispiro[5.1.5.1]tetradecan-7-one
3-(trans-4-ethylcyclohexyl)-11-(trans-4-heptylcyclohexyl)-14,14-dichlorodispiro[5.1.5.1]tetradecan-7-one
3-(trans-4-octylcyclohexyl)-11-(trans-4-propylcyclohexyl)-14,14-dichlorodispiro[5.1.5.1]tetradecan-7-one
3-(trans-4-butylcyclohexyl)-11-(trans-4-nonylcyclohexyl)-14,14-dichlorodispiro[5.1.5.1]tetradecan-7-one 3-(trans-4-decylcyclohexyl)-11-(trans-4-hexylcyclohexyl)-14,14-dichlorodispiro[5.1.5.1]tetradecan-7-one.

EXAMPLE 3

Analogously to Example 2, the 3,11-trans-dipentyl-14,14-dichlorodispiro[5.1.5.1]tetradecan-7-one, m.p. 290°, c.p. 21° is obtained from 3,11-trans-dipentyldispiro[5.1.5.1]tetradecane-7,14-dione (obtainable according to Japanese Patent No. 59-152343).

The following are prepared analogously:

3,11-trans-dimethyl-14,14-dichlorodispiro[5.1.5.1]tetradecan-7-one, K 67° I 3,11-trans-diethyl-14,14-dichlorodispiro[5.1.5.1]tetradecan-7-one 3,11-trans-dipropyl-14,14-dichlorodispiro[5.1.5.1]tetradecan-7-one, m.p. 46°, c.p. −40° (extr.)

3,11-trans-dibutyl-14,14-dichlorodispiro[5.1.5.1]tetradecan-7-one 3,11-trans-dihexyl-14,14-dichlorodispiro[5.1.5.1]tetradecan-7-one 3,11-trans-diheptyl-14,14-dichlorodispiro[5.1.5.1]tetradecan-7-one 3,11-trans-dioctyl-14,14-dichlorodispiro[5.1.5.1]tetradecan-7-one 3,11-trans-dinonyl-14,14-dichlorodispiro[5.1.5.1]tetradecan-7-one 3,11-trans-didecyl-14,14-dichlorodispiro[5.1.5.1]tetradecan-7-one 3,11-trans-dimethoxy-14,14-dichlorodispiro[5.1.5.1]tetradecan-7-one 3,11-trans-diethoxy-14,14-dichlorodispiro[5.1.5.1]tetradecan-7-one 3,11-trans-dipropoxy-14,14-dichlorodispiro[5.1.5.1]tetradecan-7-one 3,11-trans-dibutoxy-14,14-dichlorodispiro[5.1.5.1]tetradecan-7-one 3,11-trans-dipentoxy-14,14-dichlorodispiro[5.1.5.1]tetradecan-7-one 3,11-trans-dihexoxy-14,14-dichlorodispiro[5.1.5.1]tetradecan-7-one 3,11-trans-diheptoxy-14,14-dichlorodispiro[5.1.5.1]tetradecan-7-one 3,11-trans-dioctoxy-14,14-dichlorodispiro[5.1.5.1]tetradecan-7-one 3,11-trans-dinonoxy-14,14-dichlorodispiro[5.1.5.1]tetradecan-7-one 3,11-trans-didecoxy-14,14-dichlorodispiro[5.1.5.1]tetradecan-7-one 3-trans-methyl-11-trans-propyl-14,14-dichlorodispiro-[5.1.5.1]tetradecan-7-one 3-trans-propyl-11-trans-pentyl-14,14-dichlorodispiro-[5.1.5.1]tetradecan-7-one 3-trans-butyl-11-trans-ethyl-14,14-dichlorodispiro-[5.1.5.1]tetradecan-7-one 3-trans-pentyl-11-trans-heptyl-14,14-dichlorodispiro-[5.1.5.1]tetradecan-7-one 3-trans-octyl-11-trans-propyl-14,14-dichlorodispiro-[5.1.5.1]tetradecan-7-one 3-trans-propyl-11-trans-ethyl-14,14-dichlorodispiro-[5.1.5.1]tetradecan-7-one

EXAMPLE 4

A mixture of 1 mmol of 3,11-bis(trans-4-propylcyclohexyl)dispiro[5.1.5.1]tetradecane-7,14-dithione (preparable by reaction of the corresponding diketone with $P_4S_{10}$) and 25 ml of tetrahydrofuran is added at room temperature to a well stirred suspension of fresh Raney nickel in THF and stirred for 24 h at room temperature. The usual working up yields 3,11-bis(trans-4-propylcyclohexyl)dispiro[5.1.5.1]tetradecane.

The following are prepared analogously:

3,11-bis(trans-4-methylcyclohexyl)dispiro[5.1.5.1]tetradecane 3,11-bis(trans-4-ethylcyclohexyl)dispiro[5.1.5.1]tetradecane 3,11-bis(trans-4-butylcyclohexyl)dispiro[5.1.5.1]tetradecane 3,11-bis(trans-4-pentylcyclohexyl)dispiro[5.1.5.1]tetradecane 3,11-bis(trans-4-hexylcyclohexyl)dispiro[5.1.5.1]tetradecane 3,11-bis(trans-4-heptylcyclohexyl)dispiro[5.1.5.1]tetradecane 3,11-bis(trans-4-octylcyclohexyl)dispiro[5.1.5.1]tetradecane 3,11-bis(trans-4-nonylcyclohexyl)dispiro[5.1.5.1]tetradecane 3,11-bis(trans-4-decylcyclohexyl)dispiro[5.1.5.1]tetradecane 3,11-bis(trans-4-methoxycyclohexyl)dispiro[5.1.5.1]tetradecane 3,11-bis(trans-4-ethoxycyclohexyl)dispiro[5.1.5.1]tetradecane 3,11-bis(trans-4-propoxycyclohexyl)dispiro[5.1.5.1]tetradecane 3,11-bis(trans-4-butoxycyclohexyl)dispiro[5.1.5.1]tetradecane 3,11-bis(trans-4-pentoxycyclohexyl)dispiro[5.1.5.1]tetradecane 3,11-bis(trans-4-hexoxycyclohexyl)dispiro[5.1.5.1]tetradecane 3,11-bis(trans-4-heptoxycyclohexyl)dispiro[5.1.5.1]tetradecane 3,11-bis(trans-4-octoxycyclohexyl)dispiro[5.1.5.1]tetradecane 3,11-bis(trans-4-nonoxycyclohexyl)dispiro[5.1.5.1]tetradecane 3,11-bis(trans-4-decoxycyclohexyl)dispiro[5.1.5.1]tetradecane 3-(trans-4-methylcyclohexyl)-11-(trans-4-ethylcyclohexyl)-dispiro[5.1.5.1]tetradecane 3-(trans-4-ethylcyclohexyl)-11-(trans-4-pentylcyclohexyl)-dispiro[5.1.5.1]tetradecane 3-(trans-4-propylcyclohexyl)-11-(trans-4-pentylcyclohexyl)-dispiro[5.1.5.1]tetradecane 3-(trans-4-butylcyclohexyl)-11-(trans-4-ethylcyclohexyl)-dispiro[5.1.5.1]tetradecane 3-(trans-4-pentylcyclohexyl)-11-(trans-4-heptylcyclohexyl)-dispiro[5.1.5.1]tetradecane 3-(trans-4-octylcyclohexyl)-11-(trans-4-propylcyclohexyl)-dispiro[5.1.5.1]tetradecane 3-(trans-4-propylcyclohexyl)-11-(trans-4-ethylcyclohexyl)-dispiro[5.1.5.1]tetradecane

EXAMPLE 5

A mixture of 1.96 g of 3,11-trans-dipentyldispiro[5.1.5.1]tetradecane-7,14-dithione (obtainable by reaction of the corresponding diketone with $P_4S_{10}$) and 25 ml of THF are (sic) added at room temperature to a well stirred suspension of fresh Raney nickel in THF and stirred for 24 h at room temperature. After the usual working up and recrystallization from ethanol, 3,11-trans-dipentyldispiro[5.1.5.1]tetradecane is obtained with m.p. 51° and c.p. 102°.

The following are prepared analogously:

3,11-trans-dimethyldispiro[5.1.5.1]tetradecane
3,11-trans-diethyldispiro[5.1.5.1]tetradecane
3,11-trans-dipropyldispiro[5.1.5.1]tetradecane
3,11-trans-dibutyldispiro[5.1.5.1]tetradecane
3,11-trans-dihexyldispiro[5.1.5.1]tetradecane
3,11-trans-diheptyldispiro[5.1.5.1]tetradecane
3,11-trans-dioctyldispiro[5.1.5.1]tetradecane
3,11-trans-dinonyldispiro[5.1.5.1]tetradecane
3,11-trans-didecyldispiro[5.1.5.1]tetradecane
3,11-trans-dimethoxydispiro[5.1.5.1]tetradecane
3,11-trans-diethoxydispiro[5.1.5.1]tetradecane
3,11-trans-dipropoxydispiro[5.1.5.1]tetradecane
3,11-trans-dibutoxydispiro[5.1.5.1]tetradecane
3,11-trans-dipentoxydispiro[5.1.5.1]tetradecane
3,11-trans-dihexoxydispiro[5.1.5.1]tetradecane
3,11-trans-diheptoxydispiro[5.1.5.1]tetradecane
3,11-trans-dioctoxydispiro[5.1.5.1]tetradecane
3,11-trans-dinonoxydispiro[5.1.5.1]tetradecane
3,11-trans-didecoxydispiro[5.1.5.1]tetradecane 3-trans-methyl-11-trans-propyldispiro[5.1.5.1]tetradecane 3-trans-propyl-11-trans-pentyldispiro[5.1.5.1]tetradecane 3-trans-butyl-11-trans-ethyldispiro[5.1.5.1]tetradecane 3-trans-pentyl-11-trans-heptyldispiro[5.1.5.1]tetradecane 3-trans-octyl-11-trans-propyldispiro[5.1.5.1]tetradecane 3-trans-propyl-11-trans-ethyldispiro[5.1.5.1]tetradecane

EXAMPLE 6

1 mmol of 3-(trans-4-propylcyclohexyl)-11-transpentyldispiro[5.1.5.1]tetradecane-7,14-dione (obtainable according to Example 1 from trans-4-(p-propylcyclohexyl)-cyclohexanecarboxylic acid chloride and trans-4-pentylcyclohexanecarboxylic acid chloride) is stirred with 210 mg of phosphorus pentachloride in 30 ml of carbon tetrachloride for 48 hours at room temperature. After pouring onto ice-water, the organic phase is worked up. After chromatographic purification, 3-(trans-4-propylcyclohexyl)-11-trans-pentyl-14,14-dichlorodispiro[5.1.5.1]tetradecan7-one is obtained.

The following are prepared analogously:
3-(trans-4-propylcyclohexyl)-11-trans-propyl-14,14-dichlorodispiro[5.1.5.1]tetradecan-7-one
3-(trans-4-propylcyclohexyl)-11-trans-ethyl-14,14-dichlorodispiro[5.1.5.1]tetradecan-7-one
3-(trans-4-propylcyclohexyl)-11-trans-butyl-14,14-dichlorodispiro[5.1.5.1]tetradecan-7-one
3-(trans-4-butylcyclohexyl)-11-trans-butyl-14,14-dichlorodispiro[5.1.5.1]tetradecan-7-one
3-(trans-4-propylcyclohexyl)-11-trans-hexyl-14,14-dichlorodispiro[5.1.5.1]tetradecan-7-one
3-(trans-4-pentylcyclohexyl)-11-trans-pentyl-14,14-dichlorodispiro[5.1.5.1]tetradecan-7-one
3-(trans-4-ethylcyclohexyl)-11-trans-pentyl-14,14-dichlorodispiro[5.1.5.1]tetradecan-7-one
3-(trans-4-methylcyclohexyl)-11-trans-propyl-14,14-dichlorodispiro[5.1.5.1]tetradecan-7-one
3-(trans-4-pentylcyclohexyl)-11-trans-methyl-14,14-dichlorodispiro[5.1.5.1]tetradecan-7-one
3-(trans-4-heptylcyclohexyl)-11-trans-heptyl-14,14-dichlorodispiro[5.1.5.1]tetradecan-7-one.

EXAMPLE 7

According to Example 6, starting from 3-[trans-4-(p-propylcyclohexyl)cyclohexyl]-11-trans-pentyldispiro[5.1.5.1]tetradecane-7,14-dione (preparable according to Example 1 from trans-4-pentylcyclohexanecarboxylic acid chloride and trans-4-(p-propylcyclohexyl)-cyclohexylcyclohexanecarboxylic acid chloride), 3-[trans-4-(p-propylcyclohexyl)cyclohexyl]-11-trans-pentyl-14,14-dichlorodispiro[5.1.5.1]tetradecan-7-one is obtained.

The following are prepared analogously:
3-[trans-4-(p-propylcyclohexyl)cyclohexyl]-11-trans-propyl-14,14-dichlorodispiro[5.1.5.1]tetradecan-7-one
3-[trans-4-(p-propylcyclohexyl)cyclohexyl]-11-trans-ethyl-14,14-dichlorodispiro[5.1.5.1]tetradecan-7-one
3-[trans-4-(p-propylcyclohexyl)cyclohexyl]-11-trans-butyl-14,14-dichlorodispiro[5.1.5.1]tetradecan-7-one
3-[trans-4-(p-pentylcyclohexyl)cyclohexyl]-11-trans-pentyl-14,14-dichlorodispiro[5.1.5.1]tetradecan-7-one
3-[trans-4-(p-pentylcyclohexyl)cyclohexyl]-11-trans-propyl-14,14-dichlorodispiro[5.1.5.1]tetradecan-7-one
3-[trans-4-(p-ethylcyclohexyl)cyclohexyl]-11-trans-butyl-14,14-dichlorodispiro[5.1.5.1]tetradecan-7-one
3-[trans-4-(p-methylcyclohexyl)cyclohexyl]-11-trans-propyl-14,14-dichlorodispiro[5.1.5.1]tetradecan-7-one
3-[trans-4-(p-pentylcyclohexyl)cyclohexyl]-11-trans-methyl-14,14-dichlorodispiro[5.1.5.1]tetradecan-7-one
3-[trans-4-(p-heptylcyclohexyl)cyclohexyl]-11-trans-heptyl-14,14-dichlorodispiro[5.1.5.1]tetradecan-7-one.

EXAMPLE 8

Analogously to Example 4, 3-[trans-4-(p-propylcyclohexyl)cyclohexyl]-11-trans-pentyldispiro[5.1.5.1]-tetradecane is obtained starting from 3-[trans-4-(p-propylcyclohexyl)cyclohexyl]-11-trans-pentyldispiro[5.1.5.1]-tetradecane-7,14-dithione.

The following are prepared analogously:
3-(trans-4-propylcyclohexyl)-11-trans-propyldispiro[5.1.5.1]tetradecane
3-(trans-4-propylcyclohexyl)-11-trans-ethyldispiro-[5.1.5.1]tetradecane
3-(trans-4-propylcyclohexyl)-11-trans-butyldispiro-[5.1.5.1]tetradecane
3-(trans-4-butylcyclohexyl)-11-trans-butyldispiro-[5.1.5.1]tetradecane
3-(trans-4-propylcyclohexyl)-11-trans-hexyldispiro-[5.1.5.1]tetradecane
3-(trans-4-pentylcyclohexyl)-11-trans-pentyldispiro-[5.1.5.1]tetradecane
3-(trans-4-ethylcyclohexyl)-11-trans-pentyldispiro-[5.1.5.1]tetradecane
3-(trans-4-methylcyclohexyl)-11-trans-propyldispiro-[5.1.5.1]tetradecane
3-(trans-4-pentylcyclohexyl)-11-trans-methyldispiro-[5.1.5.1]tetradecane
3-(trans-4-heptylcyclohexyl)-11-trans-heptyldispiro-[5.1.5.1]tetradecane.

EXAMPLE 9

Analogously to Example 4, 3-[trans-4-(p-propylcyclohexyl)cyclohexyl-11-trans-pentyl-dispiro[5.1.5.1]-tetradecane is obtained starting from 3-[trans-4-(p-propylcyclohexyl)-11-trans-pentyldispiro[5.1.5.1]tetradecane-7,14-dithione.

The following are prepared analogously:
3-[trans-4-(p-propylcyclohexyl)cyclohexyl]-11-trans-propyldispiro[5.1.5.1]tetradecane 3-[trans-4-(p-propylcyclohexyl)cyclohexyl]-11-trans-ethyldispiro[5.1.5.1]tetradecane 3-[trans-4-(p-propylcyclohexyl)cyclohexyl]-11-trans-butyldispiro[5.1.5.1]tetradecane 3-[trans-4-(p-butylcyclohexyl)cyclohexyl]-11-trans-butyldispiro[5.1.5.1]tetradecane 3-[trans-4-(p-propylcyclohexyl)cyclohexyl]-11-trans-hexyldispiro[5.1.5.1]tetradecane 3-[trans-4-(p-pentylcyclohexyl)cyclohexyl]-11-trans-pentyldispiro[5.1.5.1]tetradecane 3-[trans-4-(p-ethylcyclohexyl)cyclohexyl]-11-trans-pentyldispiro[5.1.5.1]tetradecane 3-[trans-4-(p-methylcyclohexyl)cyclohexyl]-11-trans-propyldispiro[5.1.5.1]tetradecane 3-[trans-4-(p-pentylcyclohexyl)cyclohexyl]-11-trans-methyldispiro[5.1.5.1]tetradecane 3-[trans-4-(p-heptylcyclohexyl)cyclohexyl]-11-trans-heptyldispiro[5.1.5.1]tetradecane.

EXAMPLE 10

With atmospheric moisture being excluded, a solution of 10 g of 3,11-trans-dipentyldispiro[5.1.5.1]tetradecan-7-ol-14-one (preparable from 3,11-trans-dipentyl-[5.1.5.1]tetradecane-7,14-dione by reaction with lithium aluminum hydride) in 50 ml of dichloromethane is added at 10° C. to a solution of 5.2 g of diethylamino sulfur trifluoride in 30 ml of dichloromethane. The reaction mixture is heated to room temperature in the course of 1 hour and allowed to stand for a further hour. It is then poured onto ice and extracted with dichloromethane. After washing the organic phases, evaporating off the solvent and recrystallizing the residue, 3,11-trans-dipentyl-7-fluorodispiro[5.1.5.1]tetradecan-14-one is obtained with m.p. 53° and c.p. 116°.

The following are prepared analogously:

3,11-trans-dimethyl-7-fluorodispiro[5.1.5.1]tetradecan-14-one 3,11-trans-diethyl-7-fluorodispiro[5.1.5.1]tetradecan-14-one 3,11-trans-dipropyl-7-fluorodispiro[5.1.5.1]tetradecan-14-one 3,11-trans-dibutyl-7-fluorodispiro[5.1.5.1]tetradecan-14-one 3,11-trans-dihexyl-7-fluorodispiro[5.1.5.1]tetradecan-14-one 3,11-trans-diheptyl-7-fluorodispiro[5.1.5.1]tetradecan-14-one 3,11-trans-dioctyl-7-fluorodispiro[5.1.5.1]tetradecan-14-one 3,11-trans-dinonyl-7-fluorodispiro[5.1.5.1]tetradecan-14-one 3,11-trans-didecyl-7-fluorodispiro[5.1.5.1]tetradecan-14-one 3,11-trans-dimethoxy-7-fluorodispiro[5.1.5.1]tetradecan-14-one 3,11-trans-diethoxy-7-fluorodispiro[5.1.5.1]tetradecan-14-one 3,11-trans-dipropoxy-7-fluorodispiro[5.1.5.1]tetradecan-14-one 3,11-trans-dibutoxy-7-fluorodispiro[5.1.5.1]tetradecan-14-one 3,11-trans-dipentoxy-7-fluorodispiro[5.1.5.1]tetradecan-14-one 3,11-trans-dihexoxy-7-fluorodispiro[5.1.5.1]tetradecan-14-one 3,11-trans-diheptoxy-7-fluorodispiro[5.1.5.1]tetradecan-14-one 3,11-trans-dioctoxy-7-fluorodispiro[5.1.5.1]tetradecan-14-one 3,11-trans-dinonoxy-7-fluorodispiro[5.1.5.1]tetradecan-14-one 3,11-trans-didecoxy-7-fluorodispiro[5.1.5.1]tetradecan-14-one 3-trans-methyl-11-trans-propyl-7-fluorodispiro[5.1.5.1]tetradecan-14-one 3-trans-propyl-11-trans-pentyl-7-fluorodispiro[5.1.5.1]tetradecan-14-one 3-trans-butyl-11-trans-ethyl-7-fluorodispiro[5.1.5.1]tetradecan-14-one 3-trans-pentyl-11-trans-heptyl-7-fluorodispiro[5.1.5.1]tetradecan-14-one 3-trans-octyl-11-trans-propyl-7-fluorodispiro[5.1.5.1]tetradecan-14-one 3-trans-propyl-11-trans-ethyl-7-fluorodispiro[5.1.5.1]tetradecan-14-one 3,11-bis(trans-4-propylcyclohexyl)-7-fluorodispiro-[5.1.5.1]tetradecan-14-one 3,11-bis(trans-4-methylcyclohexyl)-7-fluorodispiro-[5.1.5.1]tetradecan-14-one 3,11-bis(trans-4-ethylcyclohexyl)-7-fluorodispiro-[5.1.5.1]tetradecan-14-one 3,11-bis(trans-4-butylcyclohexyl)-7-fluorodispiro-[5.1.5.1]tetradecan-14-one 3,11-bis(trans-4-pentylcyclohexyl)-7-fluorodispiro-[5.1.5.1]tetradecan-14-one 3,11-bis(trans-4-hexylcyclohexyl)-7-fluorodispiro-[5.1.5.1]tetradecan-14-one 3,11-bis(trans-4-heptylcyclohexyl)-7-fluorodispiro-[5.1.5.1]tetradecan-14-one 3,11-bis(trans-4-octylcyclohexyl)-7-fluorodispiro-[5.1.5.1]tetradecan-14-one 3,11-bis(trans-4-nonylcyclohexyl)-7-fluorodispiro-[5.1.5.1]tetradecan-14-one 3,11-bis(trans-4-decylcyclohexyl)-7-fluorodispiro-[5.1.5.1]tetradecan-14-one 3,11-bis(trans-4-methoxycyclohexyl)-7-fluorodispiro-[5.1.5.1]tetradecan-14-one 3,11-bis(trans-4-ethoxycyclohexyl)-7-fluorodispiro-[5.1.5.1]tetradecan-14-one 3,11-bis(trans-4-propoxycyclohexyl)-7-fluorodispiro-[5.1.5.1]tetradecan-14-one 3,11-bis(trans-4-butoxycyclohexyl)-7-fluorodispiro-[5.1.5.1]tetradecan-14-one 3,11-bis(trans-4-pentoxycyclohexyl)-7-fluorodispiro-[5.1.5.1]tetradecan-14-one 3,11-bis(trans-4-hexoxycyclohexyl)-7-fluorodispiro-[5.1.5.1]tetradecan-14-one 3,11-bis(trans-4-heptoxycyclohexyl)-7-fluorodispiro-[5.1.5.1]tetradecan-14-one 3,11-bis(trans-4-octoxycyclohexyl)-7-fluorodispiro-[5.1.5.1]tetradecan-14-one 3,11-bis(trans-4-nonoxycyclohexyl)-7-fluorodispiro-[5.1.5.1]tetradecan-14-one 3,11-bis(trans-4-decoxycyclohexyl)-7-fluorodispiro-[5.1.5.1]tetradecan-14-one 3,11-bis(4-methylphenyl)-7-fluorodispiro[5.1.5.1]-tetradecan-14-one 3,11-bis(4-ethylphenyl)-7-fluorodispiro[5.1.5.1]-tetradecan-14-one 3,11-bis(4-propylphenyl)-7-fluorodispiro[5.1.5.1]-tetradecan-14-one 3,11-bis(4-butylphenyl)-7-fluorodispiro[5.1.5.1]-tetradecan-14-one 3,11-bis(4-pentylphenyl)-7-fluorodispiro[5.1.5.1]-tetradecan-14-one 3,11-bis(4-hexylphenyl)-7-fluorodispiro[5.1.5.1]-tetradecan-14-one
3,11-bis(4-heptylphenyl)-7-fluorodispiro[5.1.5.1]-tetradecan-14-one
3,11-bis(4-octylphenyl)-7-fluorodispiro[5.1.5.1]-tetradecan-14-one
3,11-bis(4-nonylphenyl)-7-fluorodispiro[5.1.5.1]-tetradecan-14-one
3,11-bis(4-decylphenyl)-7-fluorodispiro[5.1.5.1]-tetradecan-14-one
3,11-bis(4-methoxyphenyl)-7-fluorodispiro[5.1.5.1]-tetradecan-14-one
3,11-bis(4-ethoxyphenyl)-7-fluorodispiro[5.1.5.1]-tetradecan-14-one
3,11-bis(4-propoxyphenyl)-7-fluorodispiro[5.1.5.1]-tetradecan-14-one
3,11-bis(4-butoxyphenyl)-7-fluorodispiro[5.1.5.1]-tetradecan-14-one
3,11-bis(4-pentoxyphenyl)-7-fluorodispiro[5.1.5.1]-tetradecan-14-one
3,11-bis(4-hexoxyphenyl)-7-fluorodispiro[5.1.5.1]-tetradecan-14-one
3,11-bis(4-heptoxyphenyl)-7-fluorodispiro[5.1.5.1]-tetradecan-14-one
3,11-bis(4-octoxyphenyl)-7-fluorodispiro[5.1.5.1]-tetradecan-14-one
3,11-bis(4-nonoxyphenyl)-7-fluorodispiro[5.1.5.1]-tetradecan-14-one
3,11-bis(4-decoxyphenyl)-7-fluorodispiro[5.1.5.1]-tetradecan-14-one
3-(trans-4-methylcyclohexyl)-11-(trans-4-ethylcyclohexyl)-7-fluorodispiro[5.1.5.1]tetradecan-14-one
3-(trans-4-ethylcyclohexyl)-11-(trans-4-pentylcyclohexyl)-7-fluorodispiro[5.1.5.1]tetradecan-14-one
3-(trans-4-propylcyclohexyl)-11-(trans-4-ethylcyclohexyl)-7-fluorodispiro[5.1.5.1]tetradecan-14-one
3-(trans-4-butylcyclohexyl)-11-(trans-4-ethylcyclohexyl)-7-fluorodispiro[5.1.5.1]tetradecan-14-one
3-(trans-4-hexylcyclohexyl)-11-(trans-4-ethylcyclohexyl)-7-fluorodispiro[5.1.5.1]tetradecan-14-one
3-(trans-4-ethylcyclohexyl)-11-(trans-4-heptylcyclohexyl)-7-fluorodispiro[5.1.5.1]tetradecan-14-one
3-(trans-4-octylcyclohexyl)-11-(trans-4-propylcyclohexyl)-7-fluorodispiro[5.1.5.1]tetradecan-14-one
3-(trans-4-butylcyclohexyl)-11-(trans-4-nonylcyclohexyl)-7-fluorodispiro[5.1.5.1]tetradecan-14-one
3-(trans-4-decylcyclohexyl)-11-(trans-4-hexylcyclohexyl)-7-fluorodispiro[5.1.5.1]tetradecan-14-one
3-(trans-4-propylcyclohexyl)-11-trans-pentyl-7-fluorodispiro[5.1.5.1]tetradecan-14-one
3-(trans-4-propylcyclohexyl)-11-trans-ethyl-7-fluorodispiro[5.1.5.1]tetradecan-14-one
3-(trans-4-propylcyclohexyl)-11-trans-butyl-7-fluorodispiro[5.1.5.1]tetradecan-14-one
3-(trans-4-propylcyclohexyl)-11-trans-propyl-7-fluorodispiro[5.1.5.1]tetradecan-14-one
3-(trans-4-propylcyclohexyl)-11-trans-hexyl-7-fluorodispiro[5.1.5.1]tetradecan-14-one
3-(trans-4-butylcyclohexyl)-11-trans-butyl-7-fluorodispiro[5.1.5.1]tetradecan-14-one
3-(trans-4-butylcyclohexyl)-11-trans-ethyl-7-fluorodispiro[5.1.5.1]tetradecan-14-one
3-(trans-4-butylcyclohexyl)-11-trans-propyl-7-fluorodispiro[5.1.5.1]tetradecan-14-one
3-(trans-4-butylcyclohexyl)-11-trans-pentyl-7-fluorodispiro[5.1.5.1]tetradecan-14-one
3-(trans-4-butylcyclohexyl)-11-trans-hexyl-7-fluorodispiro[5.1.5.1]tetradecan-14-one
3-(trans-4-pentylcyclohexyl)-11-trans-ethyl-7-fluorodispiro[5.1.5.1]tetradecan-14-one
3-(trans-4-pentylcyclohexyl)-11-trans-propyl-7-fluorodispiro[5.1.5.1]tetradecan-14-one
3-(trans-4-pentylcyclohexyl)-11-trans-butyl-7-fluorodispiro[5.1.5.1]tetradecan-14-one
3-(trans-4-pentylcyclohexyl)-11-trans-pentyl-7-fluorodispiro[5.1.5.1]tetradecan-14-one
3-(trans-4-pentylcyclohexyl)-11-trans-hexyl-7-fluorodispiro[5.1.5.1]tetradecan-14-one
3-(trans-4-hexylcyclohexyl)-11-trans-ethyl-7-fluorodispiro[5.1.5.1]tetradecan-14-one
3-(trans-4-hexylcyclohexyl)-11-trans-propyl-7-fluorodispiro[5.1.5.1]tetradecan-14-one
3-(trans-4-hexylcyclohexyl)-11-trans-butyl-7-fluorodispiro[5.1.5.1]tetradecan-14-one
3-(trans-4-hexylcyclohexyl)-11-trans-pentyl-7-fluorodispiro[5.1.5.1]tetradecan-14-one
3-(trans-4-hexylcyclohexyl)-11-trans-hexyl-7-fluorodispiro[5.1.5.1]tetradecan-14-one
3-(trans-4-hexylcyclohexyl)-11-trans-heptyl-7-fluorodispiro[5.1.5.1]tetradecan-14-one
3-(trans-4-ethylcyclohexyl)-11-trans-pentyl-7-fluorodispiro[5.1.5.1]tetradecan-14-one
3-(trans-4-ethylcyclohexyl)-11-trans-hexyl-7-fluorodispiro[5.1.5.1]tetradecan-14-one
3-(trans-4-ethylcyclohexyl)-11-trans-heptyl-7-fluorodispiro[5.1.5.1]tetradecan-14-one
3-(trans-4-heptylcyclohexyl)-11-trans-propyl-7-fluorodispiro[5.1.5.1]tetradecan-14-one
3-(trans-4-heptylcyclohexyl)-11-trans-butyl-7-fluorodispiro[5.1.5.1]tetradecan-14-one
3-(trans-4-heptylcyclohexyl)-11-trans-pentyl-7-fluorodispiro[5.1.5.1]tetradecan-14-one
3-(trans-4-methylcyclohexyl)-11-trans-butyl-7-fluorodispiro[5.1.5.1]tetradecan-14-one
3-(trans-4-methylcyclohexyl)-11-trans-pentyl-7-fluorodispiro[5.1.5.1]tetradecan-14-one
3-(trans-4-methylcyclohexyl)-11-trans-hexyl-7-fluorodispiro[5.1.5.1]tetradecan-14-one
3-[trans-4-(p-propylcyclohexyl)cyclohexyl]-11-trans-pentyl-7-fluoro-dispiro[5.1.5.1]tetradecan-14-one
3-[trans-4-(p-propylcyclohexyl)cyclohexyl]-11-trans-propyl-7-fluorodispiro[5.1.5.1]tetradecan-14-one
3-[trans-4-(p-propylcyclohexyl)cyclohexyl]-11-trans-ethyl-7-fluorodispiro[5.1.5.1]tetradecan-14-one
3-[trans-4-(p-propylcyclohexyl)cyclohexyl]-11-trans-butyl-7-fluorodispiro[5.1.5.1]tetradecan-14-one
3-[trans-4-(p-pentylcyclohexyl)cyclohexyl]-11-trans-pentyl-7-fluorodispiro[5.1.5.1]tetradecan-14-one
3-[trans-4-(p-pentylcyclohexyl)cyclohexyl]-11-trans-propyl-7-fluorodispiro[5.1.5.1]tetradecan-14-one
3-[trans-4-(p-ethylcyclohexyl)cyclohexyl]-11-trans-butyl-7-fluorodispiro[5.1.5.1]tetradecan-14-one
3-[trans-4-(p-methylcyclohexyl)cyclohexyl]-11-trans-propyl-7-fluorodispiro[5.1.5.1]tetradecan-14-one
3-[trans-4-(p-pentylcyclohexyl)cyclohexyl]-11-trans-methyl-7-fluorodispiro[5.1.5.1]tetradecan-14-one
3-[trans-4-(p-heptylcyclohexyl)cyclohexyl]-11-trans-heptyl-7-fluorodispiro[5.1.5.1]tetradecan-14-one

EXAMPLE 11

A mixture of 1.8 g of 3,11-dipentyl-7-oxodispiro-[5.1.5.1]tetradecane-14-dithione (obtainable from the corresponding diketone by reactiong with $P_4S_{10}$ in pyridine) and 25 ml of THF is added at room temperature to a well stirred suspension of fresh Raney nickel in THF. The mixture is stirred for 5 hours and worked up as usual. After recrystallization from ethanol, 3,11-trans-dipentyldispiro[5.1.5.1]tetradecan-7-one is obtained with m.p. 66° and c.p. 111°.

The following are prepared analogously:
3,11-trans-dimethyl-dispiro[5.1.5.1]tetradecan-7-one
3,11-trans-diethyl-dispiro[5.1.5.1]tetradecan-7-one
3,11-trans-dipropyl-dispiro[5.1.5.1]tetradecan-7-one
3,11-trans-dibutyl-dispiro[5.1.5.1]tetradecan-7-one
3,11-trans-dihexyl-dispiro[5.1.5.1]tetradecan-7-one
3,11-trans-diheptyl-dispiro[5.1.5.1]tetradecan-7-one
3,11-trans-dioctyl-dispiro[5.1.5.1]tetradecan-7-one
3,11-trans-dinonyl-dispiro[5.1.5.1]tetradecan-7-one
3,11-trans-didecyl-dispiro[5.1.5.1]tetradecan-7-one
3,11-trans-dimethoxy-dispiro[5.1.5.1]tetradecan-7-one
3,11-trans-diethoxy-dispiro[5.1.5.1]tetradecan-7-one
3,11-trans-dipropoxy-dispiro[5.1.5.1]tetradecan-7-one
3,11-trans-dibutoxy-dispiro[5.1.5.1]tetradecan-7-one
3,11-trans-dipentoxy-dispiro[5.1.5.1]tetradecan-7-one
3,11-trans-dihexoxy-dispiro[5.1.5.1]tetradecan-7-one
3,11-trans-diheptoxy-dispiro[5.1.5.1]tetradecan-7-one
3,11-trans-dioctoxy-dispiro[5.1.5.1]tetradecan-7-one
3,11-trans-dinonoxy-dispiro[5.1.5.1]tetradecan-7-one
3,11-trans-didecoxy-dispiro[5.1.5.1]tetradecan-7-one
3-trans-methyl-11-trans-propyl-dispiro[5.1.5.1]tetradecan-7-one
3-trans-propyl-11-trans-pentyl-dispiro[5.1.5.1]tetradecan-7-one
3-trans-butyl-11-trans-heptyl-dispiro[5.1.5.1]tetradecan-7-one
3-trans-pentyl-11-trans-heptyl-dispiro[5.1.5.1]tetradecan-7-one
3-trans-octyl-11-trans-propyl-dispiro[5.1.5.1]tetradecan-7-one
3-trans-propyl-11-trans-ethyl-dispiro[5.1.5.1]tetradecan-7-one
3,11-bis-(trans-4-methylcyclohexyl)-dispiro[5.1.5.1]-tetradecan-7-one
3,11-bis-(trans-4-ethylcyclohexyl)-dispiro[5.1.5.1]-tetradecan-7-one
3,11-bis-(trans-4-propylcyclohexyl)-dispiro[5.1.5.1]-tetradecan-7-one, K 338° I
3,11-bis-(trans-4-butylcyclohexyl)-dispiro[5.1.5.1]-tetradecan-7-one
3,11-bis-(trans-4-pentylcyclohexyl)-dispiro[5.1.5.1]-tetradecan-7-one
3,11-bis-(trans-4-hexylcyclohexyl)-dispiro[5.1.5.1]-tetradecan-7-one
3,11-bis-(trans-4-heptylcyclohexyl)-dispiro[5.1.5.1]-tetradecan-7-one
3,11-bis-(trans-4-octylcyclohexyl)-dispiro[5.1.5.1]-tetradecan-7-one
3,11-bis-(trans-4-nonylcyclohexyl)-dispiro[5.1.5.1]-tetradecan-7-one
3,11-bis-(trans-4-decylcyclohexyl)-dispiro[5.1.5.1]-tetradecan-7-one
3,11-bis-(trans-4-methoxycyclohexyl)-dispiro[5.1.5.1]-tetradecan-7-one
3,11-bis-(trans-4-ethoxycyclohexyl)-dispiro[5.1.5.1]-tetradecan-7-one
3,11-bis-(trans-4-propoxycyclohexyl)-dispiro[5.1.5.1]-tetradecan-7-one
3,11-bis-(trans-4-butoxycyclohexyl)-dispiro[5.1.5.1]-tetradecan-7-one
3,11-bis-(trans-4-pentoxycyclohexyl)-dispiro[5.1.5.1]-tetradecan-7-one
3,11-bis-(trans-4-hexoxycyclohexyl)-dispiro[5.1.5.1]-tetradecan-7-one
3,11-bis-(trans-4-heptoxycyclohexyl)-dispiro[5.1.5.1]-tetradecan-7-one
3,11-bis-(trans-4-octoxycyclohexyl)-dispiro[5.1.5.1]-tetradecan-7-one
3,11-bis-(trans-4-nonoxycyclohexyl)-dispiro[5.1.5.1]-tetradecan-7-one
3,11-bis-(trans-4-decoxycyclohexyl)-dispiro[5.1.5.1]-tetradecan-7-one
3-(trans-4-methylcyclohexyl)-11-(trans-4-ethylcyclohexyl)-dispiro[5.1.5.1]tetradecan-7-one
3-(trans-4-ethylcyclohexyl)-11-(trans-4-pentylcyclohexyl)-dispiro[5.1.5.1]tetradecan-7-one
3-(trans-4-propylcyclohexyl)-11-(trans-4-pentylcyclohexyl)-dispiro[5.1.5.1]tetradecan-7-one
3-(trans-4-butylcyclohexyl)-11-(trans-4-ethylcyclohexyl)-dispiro[5.1.5.1]tetradecan-7-one
3-(trans-4-pentylcyclohexyl)-11-(trans-4-heptylcyclohexyl)-dispiro[5.1.5.1]tetradecan-7-one
3-(trans-4-octylcyclohexyl)-11-(trans-4-propylcyclohexyl)-dispiro[5.1.5.1]tetradecan-7-one
3-(trans-4-propylcyclohexyl)-11-(trans-4-ethylcyclohexyl)-dispiro[5.1.5.1]tetradecan-7-one
3-(trans-4-propylcyclohexyl)-11-trans-propyldispiro-[5.1.5.1]tetradecan-7-one
3-(trans-4-propylcyclohexyl)-11-trans-ethyldispiro-[5.1.5.1]tetradecan-7-one
3-(trans-4-propylcyclohexyl)-11-trans-butyldispiro-[5.1.5.1]tetradecan-7-one
3-(trans-4-propylcyclohexyl)-11-trans-pentyldispiro-[5.1.5.1]tetradecan-7-one
3-(trans-4-propylcyclohexyl)-11-trans-hexyldispiro-[5.1.5.1]tetradecan-7-one
3-(trans-4-propylcyclohexyl)-11-trans-heptyldispiro-[5.1.5.1]tetradecan-7-one
3-(trans-4-butylcyclohexyl)-11-trans-propyldispiro-[5.1.5.1]tetradecan-7-one
3-(trans-4-butylcyclohexyl)-11-trans-ethyldispiro-[5.1.5.1]tetradecan-7-one
3-(trans-4-butylcyclohexyl)-11-trans-butyldispiro-[5.1.5.1]tetradecan-7-one
3-(trans-4-butylcyclohexyl)-11-trans-pentyldispiro-[5.1.5.1]tetradecan-7-one
3-(trans-4-butylcyclohexyl)-11-trans-hexyldispiro-[5.1.5.1]tetradecan-7-one
3-(trans-4-butylcyclohexyl)-11-trans-heptyldispiro-[5.1.5.1]tetradecan-7-one
3-(trans-4-pentylcyclohexyl)-11-trans-propyldispiro-[5.1.5.1]tetradecan-7-one
3-(trans-4-pentylcyclohexyl)-11-trans-ethyldispiro-[5.1.5.1]tetradecan-7-one
3-(trans-4-pentylcyclohexyl)-11-trans-butyldispiro-[5.1.5.1]tetradecan-7-one
3-(trans-4-pentylcyclohexyl)-11-trans-pentyldispiro-[5.1.5.1]tetradecan-7-one
3-(trans-4-pentylcyclohexyl)-11-trans-hexyldispiro-[5.1.5.1]tetradecan-7-one
3-(trans-4-pentylcyclohexyl)-11-trans-heptyldispiro-[5.1.5.1]tetradecan-7-one
3-(trans-4-ethylcyclohexyl)-11-trans-propyldispiro-[5.1.5.1]tetradecan-7-one
3-(trans-4-ethylcyclohexyl)-11-trans-ethyldispiro-[5.1.5.1]tetradecan-7-one
3-(trans-4-ethylcyclohexyl)-11-trans-butyldispiro-[5.1.5.1]tetradecan-7-one
3-(trans-4-ethylcyclohexyl)-11-trans-pentyldispiro-[5.1.5.1]tetradecan-7-one
3-(trans-4-ethylcyclohexyl)-11-trans-hexyldispiro-[5.1.5.1]tetradecan-7-one 3-(trans-4-ethylcyclohexyl)-11-trans-heptyldispiro-[5.1.5.1]tetradecan-7-one
3-(trans-4-methylcyclohexyl)-11-trans-propyldispiro-[5.1.5.1]tetradecan-7-one
3-(trans-4-methylcyclohexyl)-11-trans-ethyldispiro-[5.1.5.1]tetradecan-7-one
3-(trans-4-methylcyclohexyl)-11-trans-butyldispiro-[5.1.5.1]tetradecan-7-one
3-(trans-4-methylcyclohexyl)-11-trans-pentyldispiro-[5.1.5.1]tetradecan-7-one
3-(trans-4-methylcyclohexyl)-11-trans-hexyldispiro-[5.1.5.1]tetradecan-7-one
3-(trans-4-methylcyclohexyl)-11-trans-heptyldispiro-[5.1.5.1]tetradecan-7-one
3-(trans-4-hexylcyclohexyl)-11-trans-propyldispiro-[5.1.5.1]tetradecan-7-one
3-(trans-4-hexylcyclohexyl)-11-trans-ethyldispiro-[5.1.5.1]tetradecan-7-one
3-(trans-4-hexylcyclohexyl)-11-trans-butyldispiro-[5.1.5.1]tetradecan-7-one
3-(trans-4-hexylcyclohexyl)-11-trans-pentyldispiro-[5.1.5.1]tetradecan-7-one
3-(trans-4-hexylcyclohexyl)-11-trans-hexyldispiro-[5.1.5.1]tetradecan-7-one
3-(trans-4-hexylcyclohexyl)-11-trans-heptyldispiro-[5.1.5.1]tetradecan-7-one
3-(trans-4-heptylcyclohexyl)-11-trans-propyldispiro-[5.1.5.1]tetradecan-7-one
3-(trans-4-heptylcyclohexyl)-11-trans-ethyldispiro-[5.1.5.1]tetradecan-7-one
3-(trans-4-heptylcyclohexyl)-11-trans-butyldispiro-[5.1.5.1]tetradecan-7-one
3-(trans-4-heptylcyclohexyl)-11-trans-pentyldispiro-[5.1.5.1]tetradecan-7-one
3-(trans-4-heptylcyclohexyl)-11-trans-hexyldispiro-[5.1.5.1]tetradecan-7-one
3-(trans-4-heptylcyclohexyl)-11-trans-heptyldispiro-[5.1.5.1]tetradecan-7-one
3-[trans-4-(p-propylcyclohexyl)cyclohexyl]-11-transpentyldispiro[5.1.5.1]tetradecan-7-one
3-[trans-4-(p-propylcyclohexyl)cyclohexyl]-11-transethyldispiro[5.1.5.1]tetradecan-7-one
3-[trans-4-(p-propylcyclohexyl)cyclohexyl]-11-transpropyldispiro[5.1.5.1]tetradecan-7-one
3-[trans-4-(p-propylcyclohexyl)cyclohexyl]-11-trans-butyldispiro[5.1.5.1]tetradecan-7-one
3-[trans-4-(p-propylcyclohexyl)cyclohexyl]-11-transhexyldispiro[5.1.5.1]tetradecan-7-one
3-[trans-4-(p-propylcyclohexyl)cyclohexyl]-11-transheptyldispiro[5.1.5.1]tetradecan-7-one
3-[trans-4-(p-ethylcyclohexyl)cyclohexyl]-11-transpentyldispiro[5.1.5.1]tetradecan-7-one
3-[trans-4-(p-ethylcyclohexyl)cyclohexyl]-11-transethyldispiro[5.1.5.1]tetradecan-7-one
3-[trans-4-(p-ethylcyclohexyl)cyclohexyl]-11-transpropyldispiro[5.1.5.1]tetradecan-7-one
3-[trans-4-(p-ethylcyclohexyl)cyclohexyl]-11-transbutyldispiro[5.1.5.1]tetradecan-7-one
3-[trans-4-(p-ethylcyclohexyl)cyclohexyl]-11-transhexyldispiro[5.1.5.1]tetradecan-7-one
3-[trans-4-(p-ethylcyclohexyl)cyclohexyl]-11-transheptyldispiro[5.1.5.1]tetradecan-7-one
3-[trans-4-(p-butylcyclohexyl)cyclohexyl]-11-transpentyldispiro[5.1.5.1]tetradecan-7-one
3-[trans-4-(p-butylcyclohexyl)cyclohexyl]-11-transethyldispiro[5.1.5.1]tetradecan-7-one
3-[trans-4-(p-butylcyclohexyl)cyclohexyl]-11-transpropyldispiro[5.1.5.1]tetradecan-7-one
3-[trans-4-(p-butylcyclohexyl)cyclohexyl]-11-transbutyldispiro[5.1.5.1]tetradecan-7-one
3-[trans-4-(p-butylcyclohexyl)cyclohexyl]-11-transhexyldispiro[5.1.5.1]tetradecan-7-one
3-[trans-4-(p-butylcyclohexyl)cyclohexyl]-11-transheptyldispiro[5.1.5.1]tetradecan-7-one
3-[trans-4-(p-pentylcyclohexyl)cyclohexyl]-11-transpentyldispiro[5.1.5.1]tetradecan-7-one
3-[trans-4-(p-pentylcyclohexyl)cyclohexyl]-11-transethyldispiro[5.1.5.1]tetradecan-7-one
3-[trans-4-(p-pentylcyclohexyl)cyclohexyl]-11-transpropyldispiro[5.1.5.1]tetradecan-7-one
3-[trans-4-(p-pentylcyclohexyl)cyclohexyl]-11-transbutyldispiro[5.1.5.1]tetradecan-7-one
3-[trans-4-(p-pentylcyclohexyl)cyclohexyl]-11-transhexyldispiro[5.1.5.1]tetradecan-7-one
3-[trans-4-(p-pentylcyclohexyl)cyclohexyl]-11-transheptyldispiro[5.1.5.1]tetradecan-7-one
3-[trans-4-(p-hexylcyclohexyl)cyclohexyl]-11-transpentyldispiro[5.1.5.1]tetradecan-7-one
3-[trans-4-(p-hexylcyclohexyl)cyclohexyl]-11-transethyldispiro[5.1.5.1]tetradecan-7-one
3-[trans-4-(p-hexylcyclohexyl)cyclohexyl]-11-transpropyldispiro[5.1.5.1]tetradecan-7-one
3-[trans-4-(p-hexylcyclohexyl)cyclohexyl]-11-transbutyldispiro[5.1.5.1]tetradecan-7-one
3-[trans-4-(p-hexylcyclohexyl)cyclohexyl]-11-transhexyldispiro[5.1.5.1]tetradecan-7-one
3-[trans-4-(p-hexylcyclohexyl)cyclohexyl]-11-transheptyldispiro[5.1.5.1]tetradecan-7-one
3-[trans-4-(p-heptylcyclohexyl)cyclohexyl]-11-transpentyldispiro[5.1.5.1]tetradecan-7-one
3-[trans-4-(p-heptylcyclohexyl)cyclohexyl]-11-transethyldispiro[5.1.5.1]tetradecan-7-one
3-[trans-4-(p-heptylcyclohexyl)cyclohexyl]-11-transpropyldispiro[5.1.5.1]tetradecan-7-one
3-[trans-4-(p-heptylcyclohexyl)cyclohexyl]-11-transbutyldispiro[5.1.5.1]tetradecan-7-one
3-[trans-4-(p-heptylcyclohexyl)cyclohexyl]-11-transhexyldispiro[5.1.5.1]tetradecan-7-one
3-[trans-4-(p-heptylcyclohexyl)cyclohexyl]-11-transheptyldispiro[5.1.5.1]tetradecan-7-one

EXAMPLE 12

Analogously to Example 2, starting frrom 3,11-bis-(trans-4-propylcyclohexyl)dispiro[5.1.5.1]tetradecan-7-one, the corresponding 3,11-bis(trans-4-propylcyclohexyl)-7,7-dichlorodispiro[5.1.5.1]tetradecane is obtained with K 172° N 266° I.

The following are prepared analogously:
3,11-bis(trans-4-methylcyclohexyl)-7,7-dichlorodispiro-[5.1.5.1]tetradecane
3,11-bis(trans-4-ethylcyclohexyl)-7,7-dichlorodispiro-[5.1.5.1]tetradecane
3,11-bis(trans-4-butylcyclohexyl)-7,7-dichlorodispiro-[5.1.5.1]tetradecane
3,11-bis(trans-4-pentylcyclohexyl)-7,7-dichlorodispiro-[5.1.5.1]tetradecane
3,11-bis(trans-4-hexylcyclohexyl)-7,7-dichlorodispiro-[5.1.5.1]tetradecane
3,11-bis(trans-4-heptylcyclohexyl)-7,7-dichlorodispiro-[5.1.5.1]tetradecane
3,11-bis(trans-4-octylcyclohexyl)-7,7-dichlorodispiro-[5.1.5.1]tetradecane
3,11-bis(trans-4-nonylcyclohexyl)-7,7-dichlorodispiro-[5.1.5.1]tetradecane
3,11-bis(trans-4-decylcyclohexyl)-7,7-dichlorodispiro-[5.1.5.1]tetradecane 3,11-bis(trans-4-methoxycyclohexyl)-7,7-dichlorodispiro-[5.1.5.1]tetradecane
3,11-bis(trans-4-ethoxycyclohexyl)-7,7-dichlorodispiro-[5.1.5.1]tetradecane
3,11-bis(trans-4-propoxycyclohexyl)-7,7-dichlorodispiro-[5.1.5.1]tetradecane
3,11-bis(trans-4-butoxycyclohexyl)-7,7-dichlorodispiro-[5.1.5.1]tetradecane
3,11-bis(trans-4-pentoxycyclohexyl)-7,7-dichlorodispiro-[5.1.5.1]tetradecane
3,11-bis(trans-4-hexoxycyclohexyl)-7,7-dichlorodispiro-[5.1.5.1]tetradecane
3,11-bis(trans-4-heptoxycyclohexyl)-7,7-dichlorodispiro-[5.1.5.1]tetradecane
3,11-bis(trans-4-octoxycyclohexyl)-7,7-dichlorodispiro-[5.1.5.1]tetradecane
3,11-bis(trans-4-nonoxycyclohexyl)-7,7-dichlorodispiro-[5.1.5.1]tetradecane
3,11-bis(trans-4-decoxycyclohexyl)-7,7-dichlorodispiro-[5.1.5.1]tetradecane
3,11-bis(4-propylphenyl)-7,7-dichlorodispiro[5.1.5.1]-tetradecane
3,11-bis(4-methylphenyl)-7,7-dichlorodispiro[5.1.5.1]-tetradecane
3,11-bis(4-ethylphenyl)-7,7-dichlorodispiro[5.1.5.1]-tetradecane
3,11-bis(4-butylphenyl)-7,7-dichlorodispiro[5.1.5.1]-tetradecane
3,11-bis(4-pentylphenyl)-7,7-dichlorodispiro[5.1.5.1]-tetradecane
3,11-bis(4-hexylphenyl)-7,7-dichlorodispiro[5.1.5.1]-tetradecane
3,11-bis(4-heptylphenyl)-7,7-dichlorodispiro[5.1.5.1]-tetradecane
3,11-bis(4-octylphenyl)-7,7-dichlorodispiro[5.1.5.1]-tetradecane
3,11-bis(4-nonylphenyl)-7,7-dichlorodispiro[5.1.5.1]-tetradecane
3,11-bis(4-decylphenyl)-7,7-dichlorodispiro[5.1.5.1]-tetradecane
3,11-bis(4-methoxyphenyl)-7,7-dichlorodispiro[5.1.5.1]-tetradecane
3,11-bis(4-ethoxyphenyl)-7,7-dichlorodispiro[5.1.5.1]-tetradecane
3,11-bis(4-propoxyphenyl)-7,7-dichlorodispiro[5.1.5.1]-tetradecane
3,11-bis(4-butoxyphenyl)-7,7-dichlorodispiro[5.1.5.1]-tetradecane
3,11-bis(4-pentoxyphenyl)-7,7-dichlorodispiro[5.1.5.1]-tetradecane
3,11-bis(4-hexoxyphenyl)-7,7-dichlorodispiro[5.1.5.1]-tetradecane
3,11-bis(4-heptoxyphenyl)-7,7-dichlorodispiro[5.1.5.1]-tetradecane
3,11-bis(4-octoxyphenyl)-7,7-dichlorodispiro[5.1.5.1]-tetradecane
3,11-bis(4-nonoxyphenyl)-7,7-dichlorodispiro[5.1.5.1]-tetradecane
3,11-bis(4-decoxyphenyl)-7,7-dichlorodispiro[5.1.5.1]-tetradecane
3,11-trans-dipropyl-7,7-dichlorodispiro[5.1.5.1]tetradecane
3,11-trans-dimethyl-7,7-dichlorodispiro[5.1.5.1]tetradecane
3,11-trans-diethyl-7,7-dichlorodispiro[5.1.5.1]tetradecane
3,11-trans-dibutyl-7,7-dichlorodispiro[5.1.5.1]tetradecane
3,11-trans-dipentyl-7,7-dichlorodispiro[5.1.5.1]tetradecane
3,11-trans-dihexyl-7,7-dichlorodispiro[5.1.5.1]tetradecane
3,11-trans-diheptyl-7,7-dichlorodispiro[5.1.5.1]tetradecane
3,11-trans-dioctyl-7,7-dichlorodispiro[5.1.5.1]tetradecane
3,11-trans-dinonyl-7,7-dichlorodispiro[5.1.5.1]tetradecane
3,11-trans-didecyl-7,7-dichlorodispiro[5.1.5.1]tetradecane
3,11-trans-dimethoxy-7,7-dichlorodispiro[5.1.5.1]tetradecane
3,11-trans-diethoxy-7,7-dichlorodispiro[5.1.5.1]tetradecane
3,11-trans-dipropoxy-7,7-dichlorodispiro[5.1.5.1]tetradecane
3,11-trans-dibutoxy-7,7-dichlorodispiro[5.1.5.1]tetradecane
3,11-trans-dipentoxy-7,7-dichlorodispiro[5.1.5.1]tetradecane
3,11-trans-dihexoxy-7,7-dichlorodispiro[5.1.5.1]tetradecane
3,11-trans-diheptoxy-7,7-dichlorodispiro[5.1.5.1]tetradecane
3,11-trans-dioctoxy-7,7-dichlorodispiro[5.1.5.1]tetradecane
3,11-trans-dinonoxy-7,7-dichlorodispiro[5.1.5.1]tetradecane
3,11-trans-didecoxy-7,7-dichlorodispiro[5.1.5.1]tetradecane
3-(trans-4-methylcyclohexyl)-11-(trans-4-ethylcyclohexyl)-7,7-dichlorodispiro[5.1.5.1]tetradecane
3-(trans-4-ethylcyclohexyl)-11-(trans-4-pentylcyclohexyl)-7,7-dichlorodispiro[5.1.5.1]tetradecane
3-(trans-4-propylcyclohexyl)-11-(trans-4-ethylcyclohexyl)-7,7-dichlorodispiro[5.1.5.1]tetradecane
3-(trans-4-butylcyclohexyl)-11-(trans-4-ethylcyclohexyl)-7,7-dichlorodispiro[5.1.5.1]tetradecane
3-(trans-4-hexylcyclohexyl)-11-(trans-4-ethylcyclohexyl)-7,7-dichlorodispiro[5.1.5.1]tetradecane
3-(trans-4-ethylcyclohexyl)-11-(trans-4-heptylcyclohexyl)-7,7-dichlorodispiro[5.1.5.1]tetradecane
3-(trans-4-octylcyclohexyl)-11-(trans-4-propylcyclohexyl)-7,7-dichlorodispiro[5.1.5.1]tetradecane
3-(trans-4-butylcyclohexyl)-11-(trans-4-nonylcyclohexyl)-7,7-dichlorodispiro[5.1.5.1]tetradecane
3-(trans-4-decylcyclohexyl)-11-(trans-4-hexylcyclohexyl)-7,7-dichlorodispiro[5.1.5.1]tetradecane
3-trans-methyl-11-trans-propyl-7,7-dichlorodispiro-[5.1.5.1]tetradecane
3-trans-propyl-11-trans-pentyl-7,7-dichlorodispiro-[5.1.5.1]tetradecane
3-trans-butyl-11-trans-ethyl-7,7-dichlorodispiro-[5.1.5.1]tetradecane
3-trans-pentyl-11-trans-hexyl-7,7-dichlorodispiro-[5.1.5.1]tetradecane
3-trans-octyl-11-trans-pentyl-7,7-dichlorodispiro-[5.1.5.1]tetradecane
3-trans-propyl-11-trans-ethyl-7,7-dichlorodispiro-[5.1.5.1]tetradecane The examples which follow relate to liquid-crystalline phases.

Example A:
A liquid-crystalline phase consisting of:
17% p-trans-4-propylcyclohexylbenzonitrile,
16% trans-1-p-ethoxyphenyl-4-propylcyclohexane, 23% p-trans-4-pentylcyclohexylbenzonitrile,
12% trans-1-p-butoxyphenyl-4-propylcyclohexane,
17% 4-ethyl-4'-(trans-4-pentylcyclohexyl)biphenyl and
15% 3,11-bis(trans-4-propylcyclohexyl)-14,14-dichlorodispiro[5.1.5.1]tetradecan-7-one has a c.p. of 85°.

Example B:
A liquid-crystalline phase consisting of
15% p-trans-4-propylcyclohexylbenzonitrile,
11% p-trans-4-butylcyclohexylbenzonitrile,
21% p-trans-4-pentylcyclohexylbenzonitrile,
15% 3,11-trans-dipentyl-14,14-dichlorodispiro[5.1.5.1]tetradecan-7-one,
21% 4-ethyl-4'-(trans-4-pentylcyclohexyl)biphenyl,
12% 4-(trans-4-pentylcyclohexyl-4'-(trans-4-propylcyclohexyl)-biphenyl and
5% 4-cyano-4'-trans-4-pentylcyclohexyl)biphenyl has a c.p. of 98°.

We claim:
1. A dispirotetradecane of the formula I

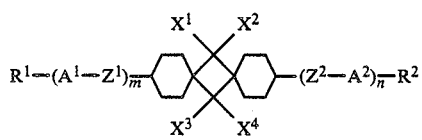

wherein
R$^1$ and R$^2$ are each independently alkyl containing 1 to 12 carbon atoms wherein one or more non-adjacent CH$_2$ groups may also be replaced by —O—, —CO—, —CO—O—, —O—CO—, —O—COO— and/or —CH=CH— (trans), and one of the radicals R$^1$ and R$^2$ can also be H, F, Cl, Br, I, CN, NO$_2$, or NCS, A$^1$ and A$^2$ are each independently trans-1,4-cyclohexylene wherein one or two nonadjacent CH$_2$ groups may be replaced by —O— and/or —S—, or 1,4-phenylene wherein one or more CH groups may also be replaced by N, with it also being possible optionally for A$^1$ and A$^2$ to be substituted laterally or axially by F, Cl, CN, or CH$_3$, Z$^1$ and Z$^2$ are each independently —CO—O—, —O—CO—, —CH$_2$CH$_2$—, —CH$_2$O—, —OCH$_2$— or a single bond, m and n are each 0, 1 or 2, (m+n) 0, 1 or 2, X$^1$, X$^2$, X$^3$ and X$^4$ are each independently H, F, Cl or CN, and one or both of the groups CX$^1$X$^2$ and CX$^3$X$^4$ may also be C=O, with the proviso that (m+n) is 1 or 2 if both groups CX$^1$X$^2$ and CX$^3$X$^4$ are C=O.

2. A compound of claim 1, wherein X$^1$–X$^4$ are all H.

3. A compound of claim 1, wherein (m+n) is O.

4. A compound of claim 1, wherein R$^1$ and R$^2$ are each independently alkyl or alkoxy.

5. A compound of claim 1, wherein X$^1$ and X$^2$ are each H and at least one of X$^3$ and X$^4$ is not H.

6. A compound of claim 1, wherein X$^1$ and X$^2$ are C=O.

7. In a liquid crystalline phase comprising at least two liquid crystal components, the improvement wherein at least one component is a dispirotetradecane of claim 1.

8. A liquid-crystalline phase of claim 7 having an optical anisotropy Δn less than or equal to 0.09.

9. In a liquid-crystalline display element comprising a liquid crystal phase, the improvement wherein the phase is one of claim 7.

10. In a liquid-crystalline display element comprising a liquid crystal phase, the improvement wherein the phase is one of claim 8.

11. In an electrooptical display element comprising a liquid crystal phase, the improvement wherein the phase is one of claim 7.

12. In an electrooptical display element comprising a liquid crystal phase, the improvement wherein the phase is one of claim 8.

* * * * *